United States Patent
Kim et al.

(10) Patent No.: US 11,541,215 B2
(45) Date of Patent: Jan. 3, 2023

(54) MULTIMODAL ENDOSCOPE AND METHODS OF USE

(71) Applicant: TRITON SYSTEMS, INC., Chelmsford, MA (US)

(72) Inventors: Yoojeong Kim, Sudbury, MA (US); Sarena Horava, Medway, MA (US); Anant Singh, Woburn, MA (US)

(73) Assignee: TRITON SYSTEMS, INC., Chelmsford, MA (US)

( * ) Notice: Subject to any disclaimer, the term of this patent is extended or adjusted under 35 U.S.C. 154(b) by 330 days.

(21) Appl. No.: 16/581,925

(22) Filed: Sep. 25, 2019

(65) Prior Publication Data

US 2020/0094030 A1    Mar. 26, 2020

Related U.S. Application Data

(60) Provisional application No. 62/736,140, filed on Sep. 25, 2018.

(51) Int. Cl.
*A61B 1/227* (2006.01)
*A61M 31/00* (2006.01)
(Continued)

(52) U.S. Cl.
CPC ......... *A61M 31/00* (2013.01); *A61B 1/00066* (2013.01); *A61B 1/00165* (2013.01);
(Continued)

(58) Field of Classification Search
CPC .......... A61M 31/00; A61M 2205/3306; A61B 1/00066; A61B 1/00165; A61B 1/05; A61B 1/00195; A61B 1/00154; A61B 1/00087; A61B 1/00108; A61B 1/00133; A61B 1/00052; A61B 1/00068; A61B 1/015
See application file for complete search history.

(56) References Cited

U.S. PATENT DOCUMENTS 3,596,653 A * 8/1971 Hotchkiss ............ A61B 1/2275
                                              600/200
4,641,663 A * 2/1987 Juhn ..................... A61B 1/227
                                              141/27

(Continued)

OTHER PUBLICATIONS

International Search Report and Written Opinion for PCT/US2019/52828 dated Dec. 11, 2019.

*Primary Examiner* — Alexandra L Newton
*Assistant Examiner* — Shankar Raj Ghimire
(74) *Attorney, Agent, or Firm* — DLA Piper (US) LLP

(57) ABSTRACT

An endoscope may include a needle and a scope, which may optionally be contained in an elongated shaft. The endoscope may further include a handle comprising at least one button, a visualization component, a reservoir configured to contain a composition, and a dispensing mechanism. The at least one button, the needle, the reservoir, and the dispensing mechanism may be operably linked to cause the composition to be dispensed from the reservoir through the needle to a portion of an ear. A method for using such an endoscope may include inserting the endoscope into a portion of an ear, using the visualization component to visualize the portion of the ear, and pressing the at least one button to dispense the composition from the reservoir through the needle to the portion of the ear.

20 Claims, 27 Drawing Sheets

(51) Int. Cl.
*A61B 1/00* (2006.01)
*A61B 1/05* (2006.01)

(52) U.S. Cl.
CPC ............ *A61B 1/00195* (2013.01); *A61B 1/05* (2013.01); *A61B 1/227* (2013.01); *A61M 2205/3306* (2013.01); *A61M 2210/0662* (2013.01)

(56) References Cited

U.S. PATENT DOCUMENTS

| | | | |
|---|---|---|---|
| 5,388,588 A | | 2/1995 | Nabai et al. |
| 5,556,416 A | | 9/1996 | Clark et al. |
| 5,714,832 A | * | 2/1998 | Shirrod .................. A61B 1/227 |
| | | | 310/328 |
| 5,847,832 A | * | 12/1998 | Liskow .............. G01B 11/2527 |
| | | | 356/613 |
| 5,879,289 A | | 3/1999 | Yarush et al. |
| 5,899,915 A | | 5/1999 | Saadat |
| 5,916,150 A | * | 6/1999 | Sillman .................. A61B 10/06 |
| | | | 600/184 |
| 5,928,137 A | | 7/1999 | Green |
| 6,387,043 B1 | | 5/2002 | Yoon |
| 6,390,975 B1 | * | 5/2002 | Walls ..................... A61B 1/227 |
| | | | 600/200 |
| 8,062,216 B2 | * | 11/2011 | Raghuprasad ......... A61B 1/227 |
| | | | 600/200 |
| 2001/0025174 A1 | | 9/2001 | Daniel et al. |
| 2003/0171655 A1 | * | 9/2003 | Newman ................ A61B 1/227 |
| | | | 600/200 |
| 2004/0162572 A1 | | 8/2004 | Sauer |
| 2006/0025813 A1 | | 2/2006 | Shelton et al. |
| 2007/0106204 A1 | * | 5/2007 | Fedenia .............. A61M 1/7413 |
| | | | 604/28 |
| 2007/0167918 A1 | * | 7/2007 | Reed ..................... A61M 1/774 |
| | | | 604/187 |
| 2007/0203396 A1 | | 8/2007 | McCutcheon et al. |
| 2008/0091104 A1 | | 4/2008 | Abraham |
| 2008/0243162 A1 | | 10/2008 | Shibata et al. |
| 2008/0262510 A1 | * | 10/2008 | Clifford .................. A61N 1/30 |
| | | | 606/109 |
| 2009/0287236 A1 | | 11/2009 | Bakos et al. |
| 2010/0081965 A1 | | 4/2010 | Mugan et al. |
| 2011/0015489 A1 | * | 1/2011 | Raghuprasad ......... A61B 1/227 |
| | | | 600/187 |
| 2011/0282324 A1 | | 11/2011 | Kurokawa et al. |
| 2011/0282381 A1 | * | 11/2011 | Cronin ................ A61M 5/1407 |
| | | | 606/213 |
| 2012/0253267 A1 | * | 10/2012 | Reed ..................... A61M 1/774 |
| | | | 604/28 |
| 2013/0144186 A1 | | 6/2013 | Furlong |
| 2013/0324910 A1 | | 12/2013 | Ohri et al. |
| 2014/0309655 A1 | | 10/2014 | Gal et al. |
| 2015/0105796 A1 | | 4/2015 | Grace |
| 2016/0279321 A1 | * | 9/2016 | Bansal .................. A61B 1/126 |
| 2016/0346511 A1 | * | 12/2016 | Cohen ..................... A61M 1/76 |
| 2016/0367119 A1 | | 12/2016 | Ouyang et al. |
| 2017/0188794 A1 | | 7/2017 | Ouyang et al. |
| 2018/0125345 A1 | * | 5/2018 | Rebella .............. A61B 1/00082 |
| 2018/0153543 A1 | | 6/2018 | Schneider et al. |
| 2018/0303314 A1 | * | 10/2018 | Noyes ................ A61B 1/00124 |
| 2019/0151574 A1 | * | 5/2019 | Mangold ................ B05B 11/02 |
| 2020/0078509 A1 | * | 3/2020 | Bryning ................. A61B 1/227 |
| 2020/0094030 A1 | * | 3/2020 | Kim .................. A61B 1/00133 |
| 2020/0306463 A1 | * | 10/2020 | Shahaf ..................... A61P 3/04 |
| 2021/0228237 A1 | * | 7/2021 | de Juan ................. A61B 1/227 |

* cited by examiner

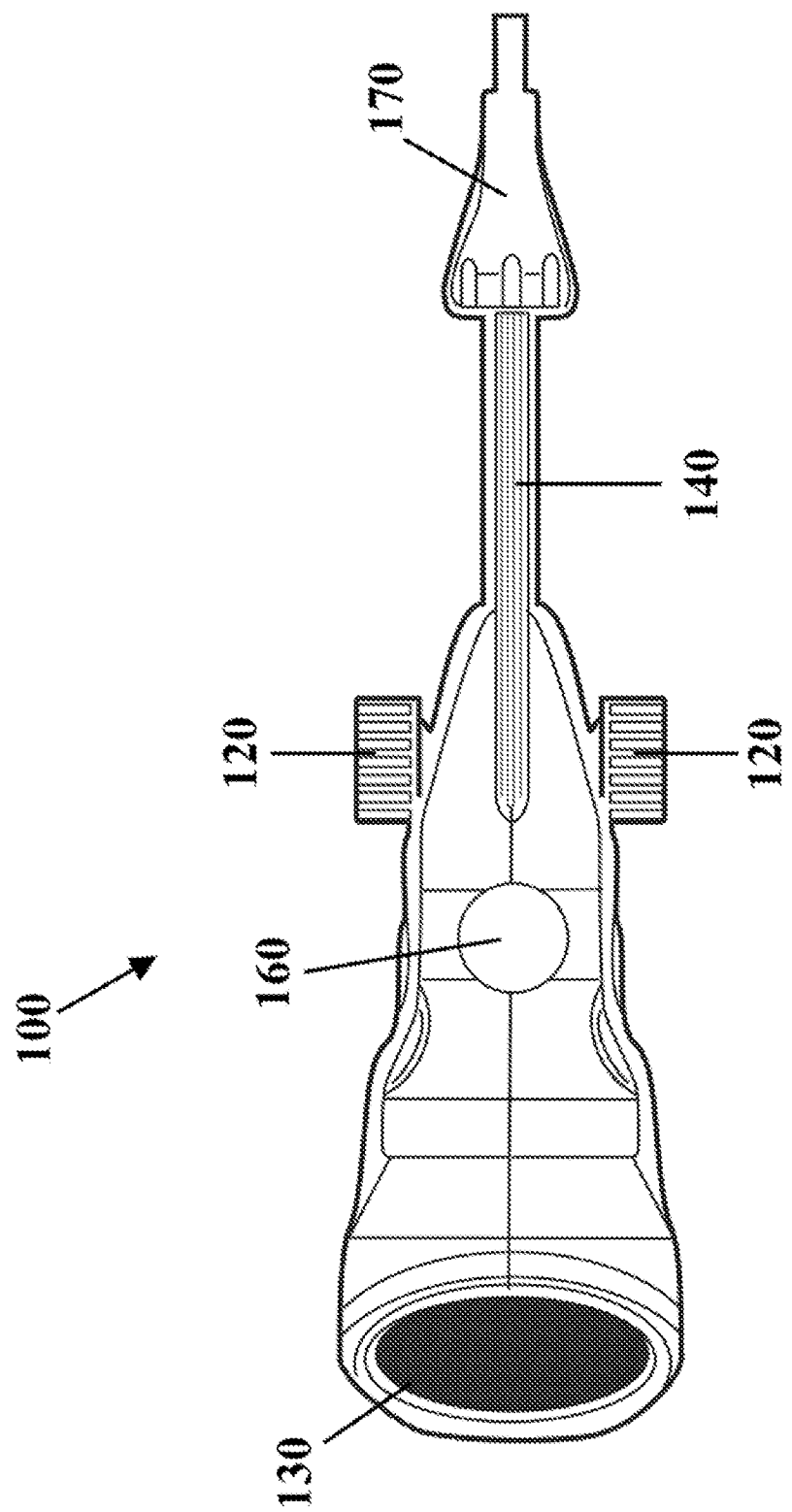

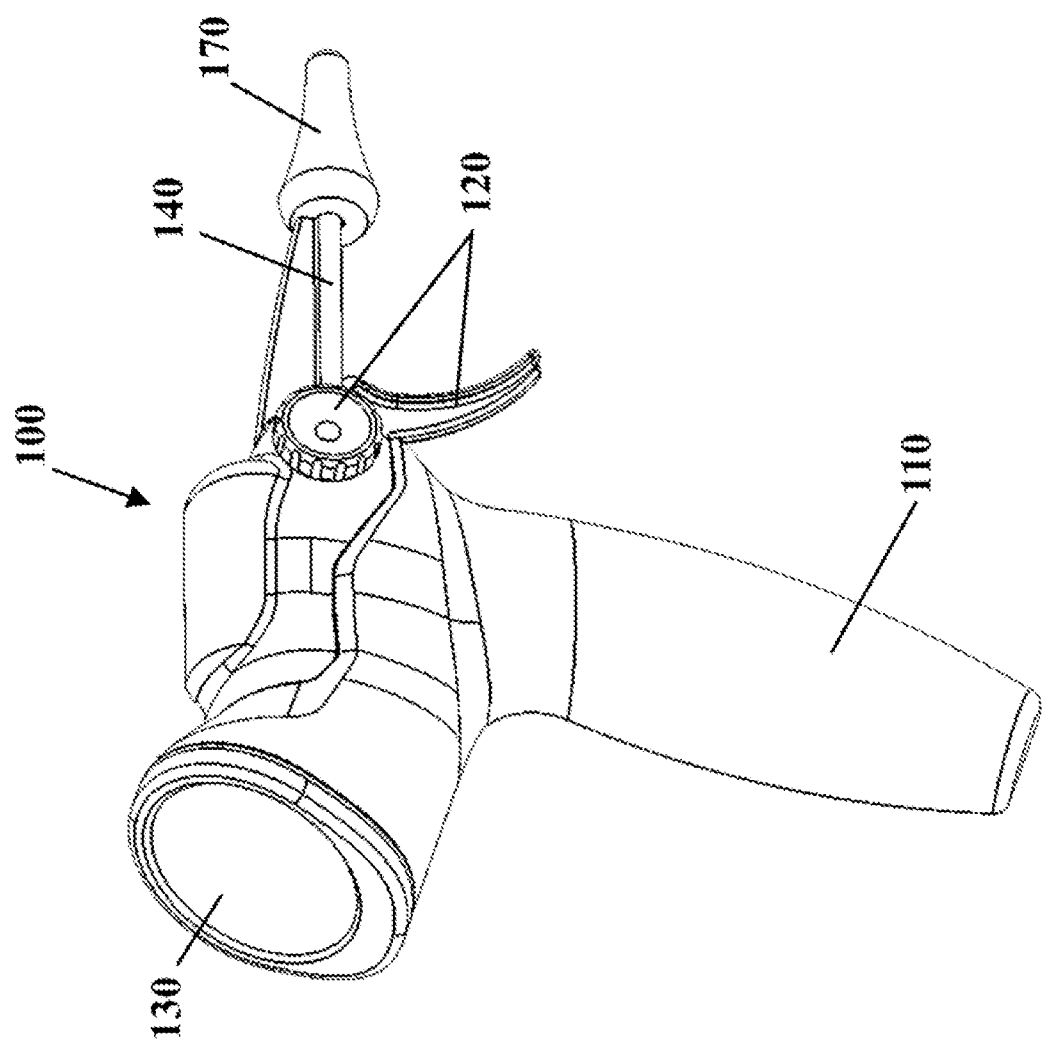

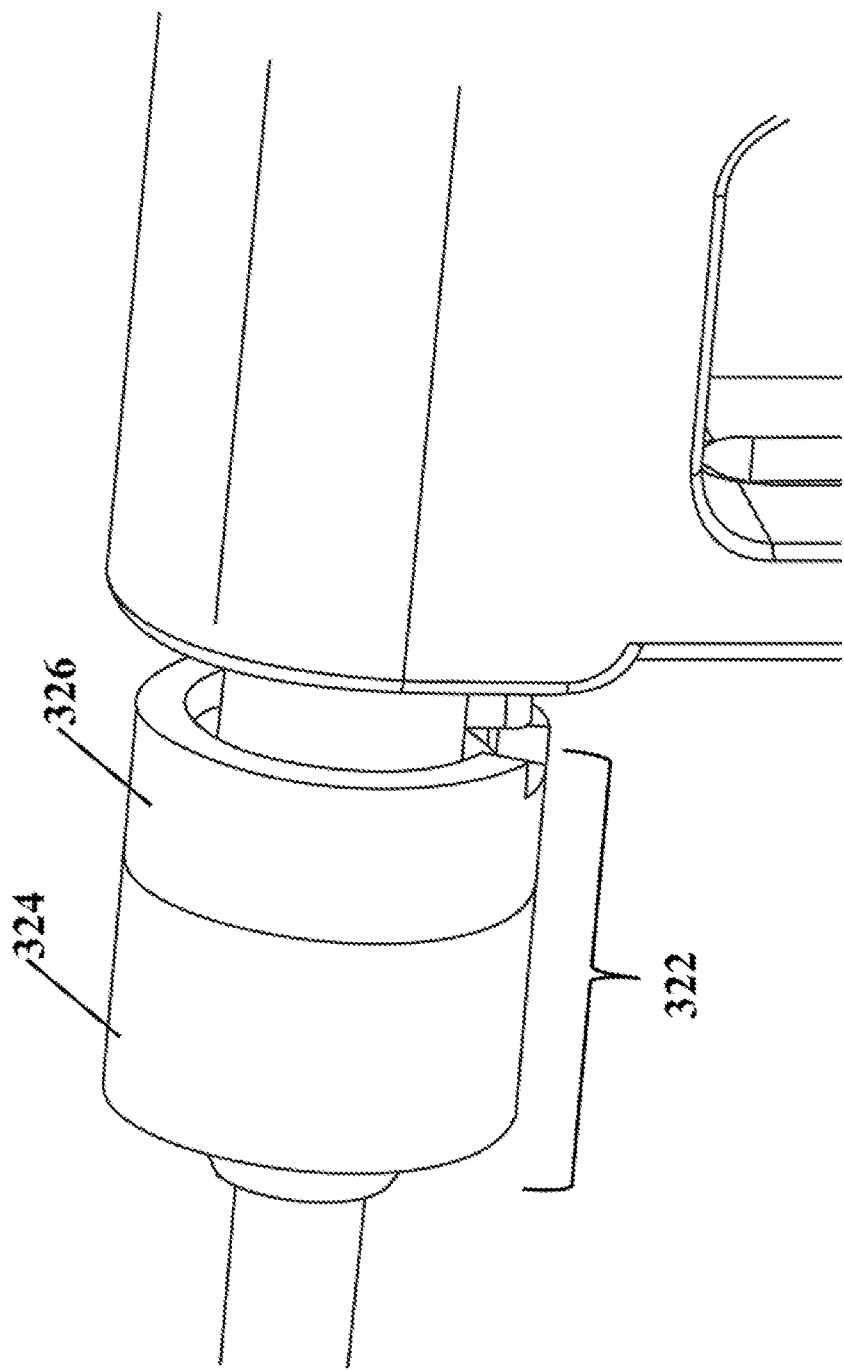

MULTIMODAL ENDOSCOPE AND METHODS OF USE

CROSS-REFERENCE TO RELATED APPLICATIONS

This application claims priority to and benefit of U.S. Provisional Application Ser. No. 62/736,140, filed Sep. 25, 2018, entitled "Multimodal Endoscope and Methods of Use," which is incorporated herein by reference in its entirety.

GOVERNMENT INTERESTS

This invention was made with government support under Contract W81XWH-18-C-0057 and Contract W81XWH-19-C-0041 awarded by the Defense Health Agency. The government has certain rights in the invention.

BACKGROUND

Hearing loss and tinnitus are significant public health issues in the United States and worldwide, with a considerably higher prevalence of these disorders among military personnel. Impairment of the auditory system is the second most prevalent bodily system injury among veterans. Hearing loss impacts operational effectiveness, medical readiness, and quality of life. Such conditions negatively impact long-term health by compromising sleep quality, reducing independence, and increasing frustration, irritability, stress, depression, and/or anxiety. Noise-induced hearing loss (NIHL) has a higher incidence rate among service members due to extremely harsh noise hazards in a military setting such as weapons training, artillery, aircrafts, manufacturing, construction, maintenance, and blasts. Other civilian industrial workers may also be subjected to such noise hazards. Noise levels in military operations can be significantly higher than industrial noise levels, and soldiers are often required to remain in the noisy environment, increasing their exposure.

Blast-induced tinnitus and blast-induced hearing loss are particularly critical causes of disability in war veterans due to increasing incidence of improvised explosive devices (IEDs) and rocket-propelled grenade attacks. Hearing loss is a common co-morbidity with traumatic brain injury (TBI), with 33% suffering acute hearing loss, 43% suffering sub-acute hearing loss, and 9% suffering chronic hearing loss. Furthermore, over 90% of veterans that had blast-induced TBI reported tinnitus, with over 60% still reporting tinnitus several months post-blast event. There is a strong correlation between NIHL and tinnitus, with an estimated 80% of NIHL suffers also reporting tinnitus. Despite efforts to improve military hearing conservation programs, 10-18% of service members enrolled in such programs are still diagnosed with significant threshold shifts in their hearing. In addition, in 2012, annual compensation and care of hearing loss and auditory system injuries for over 1.8 million veterans was estimated at $1.2 billion. In 2016, more than 1.45 million and 1 million veterans received disability compensation for hearing loss and tinnitus, respectively.

Inner ear disorders such as tinnitus and sudden hearing loss, when associated with acute noise or blast exposure, require timely intervention. For timely management of acute acoustic trauma, local drug delivery to the middle ear requires clinical expertise and specialized instrumentation. However, military members have limited access to such specialized medical care while deployed in remote settings, where many of these noise-related injuries are sustained. Thus, there is an unmet need for a device for administering drugs intratympanically in a safe and easy manner.

SUMMARY

The instant disclosure relates generally to a multimodal endoscope and methods of use. In one embodiment, an endoscope may comprise a needle and a scope, a handle comprising at least one button, a visualization component, a reservoir configured to contain a composition, and a dispensing mechanism. In some embodiments, the at least one button, the needle, the reservoir, and the dispensing mechanism may be operably linked to cause the composition to be dispensed from the reservoir through the needle to a portion of an ear.

In another embodiment, a method for using such an endoscope may include inserting the endoscope into a portion of an ear, using the visualization component to visualize the portion of the ear, and pressing the at least one button to dispense the composition from the reservoir through the needle to the portion of the ear. In certain embodiments, the at least one button may comprise a first button and a second button. In one embodiment, the first button is a wheel configured to facilitate advancing the needle and retracting the needle, and wherein the second button is a trigger configured to dispense the composition. Further embodiments of the instant disclosure are described herein.

BRIEF DESCRIPTION OF THE DRAWINGS

FIG. 7B illustrates a top view of the endoscope of FIG. 7A, in accordance with the present disclosure.

FIG. 12A illustrates an alternative embodiment of an endoscope that includes a stop component, in accordance with the present disclosure.

FIG. 17D shows a close-up view of a portion of the endoscope of FIG. 17A, in accordance with the present disclosure.

DETAILED DESCRIPTION

Figure 1:
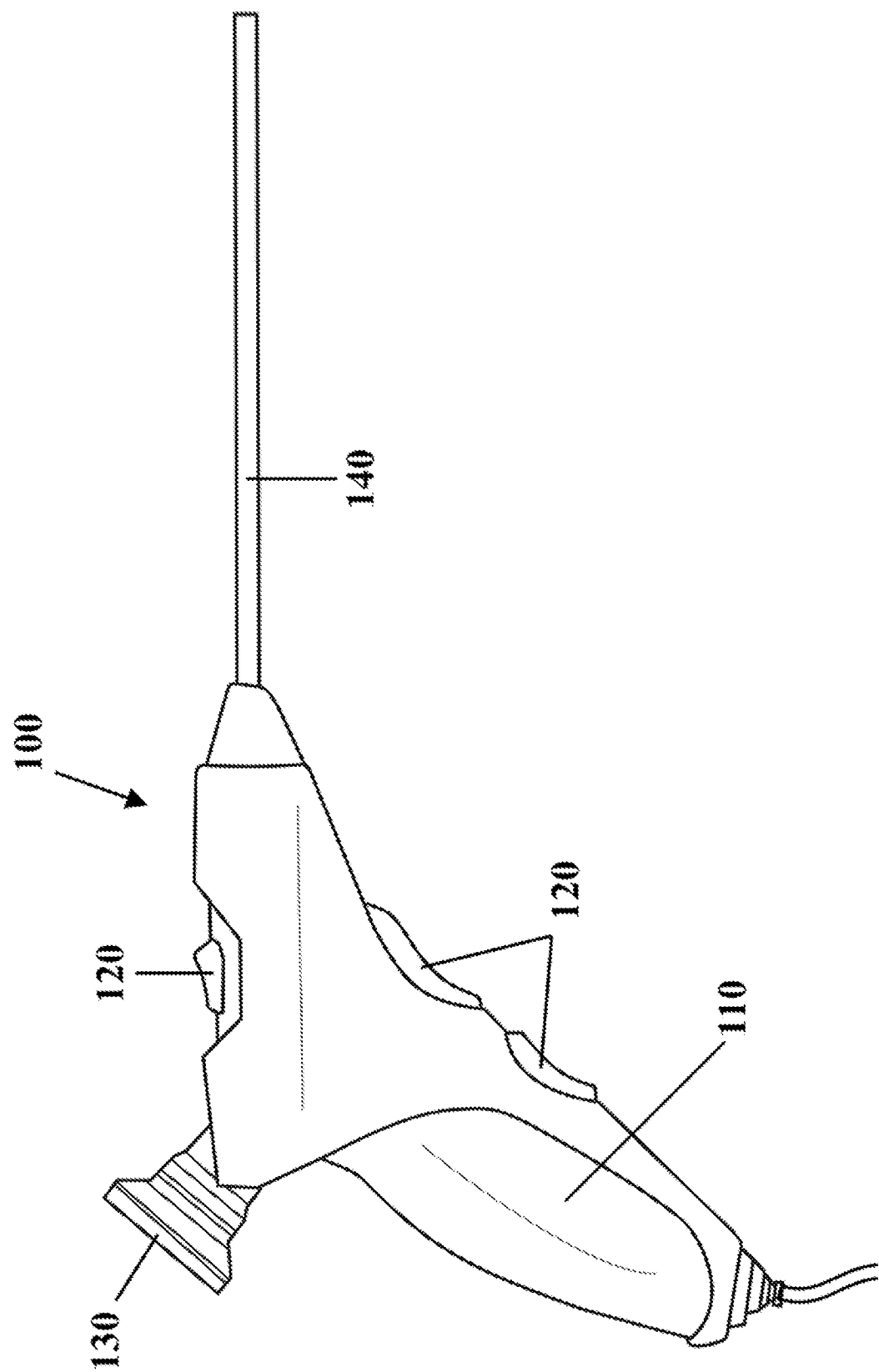
FIG. 1 illustrates an embodiment of an endoscope, in accordance with the present disclosure.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to an "agent" is a reference to one or more agents and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of."

Inner ear disorders such as tinnitus and sudden hearing loss, when associated with acute noise or blast exposure, require timely intervention. For timely management of acute acoustic trauma, local drug delivery to the middle ear requires clinical expertise and specialized instrumentation. However, military members have limited access to such specialized medical care while deployed in remote settings, where many of these noise-related injuries are sustained. Thus, there is an unmet need for a device for administering drugs intratympanically in a safe and easy manner.

Inner ear diseases are not effectively treated by systemic drug administration (parenteral and oral routes) mainly because the blood-perilymph barrier (BPLB) reduces transport between plasma and the inner ear fluids. Systemic drugs may also have unwanted side effects, further impeding their desirability for inner ear diseases. Additionally, local drug delivery methods that maximize drug concentration in the inner ear while minimizing systemic exposure are being developed to treat inner ear diseases. Topical treatments applied through the external auditory canal, such as ear drops, are limited to outer ear and some middle ear diseases with perforated eardrums. Topical treatments are not effective for treating inner ear diseases due to the barriers of the tympanic membrane (eardrum), bone, round window, and oval window between the outer and inner ear. Two main approaches for local delivery to the inner ear are: (i) intratympanic administration, in which drugs are administered to the middle ear; and (ii) intracochlear administration, in which drugs are administered directly to the inner ear. Intratympanic administration is minimally invasive and relies on the diffusion of the drug through the round window to reach the inner ear. Intracochlear administration is highly invasive but allows for direct access to the cochlea. The devices and methods herein may work particularly well for intratympanic administration, as this method of administration is adaptable for application outside the clinical setting, but both methods are contemplated throughout the disclosure and the devices and methods disclosed herein may be appropriate for either method.

The instant disclosure is directed to a multimodal endoscope and methods of use. The devices and methods contemplated herein are configured to combine three key functions: (1) transcanal imaging for visualization of a portion of the ear, such as the tympanic membrane; (2) optionally, the application of a topical composition such as a topical anesthetic; and (3) administration of aqueous or viscous compositions to a portion of the ear, including intratympanic administration of such compositions, for executing transtympanic injections with a single device and a single operator. The use of a single device may improve handling for the operator and minimize risk for the patient.

Without wishing to be bound by theory, the devices and methods contemplated herein may provide a number of advantages, including excellent visualization of components of the ear, such as the ear canal and the tympanic membrane by employing imaging techniques such as high-definition imaging, a wide field of view, enhanced optics, and a device-integrated display screen. Advantages may also include portability for use in remote locations, which requires a compact, battery-powered device without external monitors. The devices and methods disclosed herein may also offer ease of use, with a single instrument for visualization and composition delivery. Further advantages may include the ease of composition administration, with precise delivery of compositions at specified flow rates and doses, well-suited for aqueous and viscous formulations, and a quantified volume of composition dispensed for documentation. In addition, advantages may include improved safety and minimized user errors, facilitated by an optional speculum or stop component for safe placement and device stabilization, and an optional two-laser system for needle positioning and measurements of the distance to the tympanic membrane. Furthermore, optional sensors and bevel indicators may be used to detect the puncture of a portion of the ear and the proper positioning of a needle within the portion of the ear, respectively.

In an embodiment, an endoscope may comprise a needle and a scope, a handle comprising at least one button, a visualization component, a reservoir configured to contain a composition, and a dispensing mechanism. In an embodiment, the scope may comprise at least one lens and a light transmission component (e.g., a fiber optic light transmission component). In certain embodiments, the scope may comprise multiple lenses. In some embodiments, the scope may include an imaging chip or sensor, and/or a fiber optic cable. In one embodiment, the scope may be flexible, while in another embodiment, the scope may be rigid. In certain embodiments, the scope may be optical, while in other embodiments, the scope may be digital. In an embodiment, a flexible scope may be digital, while in other embodiments, a rigid scope may be optical and/or digital.

In some embodiments, the needle may be selected from the group consisting of a sharp needle, a beveled needle, a blunt needle, a catheter, or any combination thereof. In a non-limiting example, the needle may have a gauge size of between about 18 gauge and about 27 gauge. The needle may have a gauge size of, for example, about 18 gauge, about 19 gauge, about 20 gauge, about 21 gauge, about 22 gauge, about 23 gauge, about 24 gauge, about 25 gauge, about 26 gauge, about 27 gauge, or any range between any two of these values, including endpoints. In certain embodiments, the needle may be detachable and disposable, while in other embodiments the needle may be rigidly attached, reusable, sterilizable, or any combination thereof. In one embodiment, the needle may have one or more colored bands at one end. In some embodiments, the one or more colored bands may be configured to act as a bevel indicator, and may be configured to allow a user to visualize the colored band passing through the portion of the ear, such as the tympanic membrane.

In some embodiments, the at least one button may include 1 button, 2 buttons, 3 buttons, 4 buttons, 5 buttons, 6 buttons, 7 buttons, 8 buttons, 9 buttons, 10 buttons, or any range between any two of these values, including endpoints. In certain embodiments, the at least one button may be configured to facilitate a function. The function may be, for example, advancing the needle, retracting the needle, dispensing the composition, or any combination thereof. In some embodiments, the at least one button may be a push-button, a wheel, a trigger, any combination thereof, or any other button type known in the art. In one embodiment, the at least one button may comprise a first button and a second button, and the first button and the second button may each independently be selected from a push-button, a wheel, a trigger, and combinations thereof. In an embodiment, the first button may be a wheel configured to facilitate advancing and/or retracting the needle, and the second button may be a trigger configured to dispense the composition. In some embodiments, the needle may be configured to be selectively deployed and retracted by pressing the at least one button of the handle.

In certain embodiments, the handle may further comprise a camera. In an embodiment, the camera may be a high-definition (HD) camera. In some embodiments, the camera may be coupled or connected to the visualization component of the endoscope, either with wires or wirelessly. In other embodiments, the handle may further comprise a light source. The light source may include, for example, an LED light. In some embodiments, the light source may be external and/or battery-powered.

In some embodiments, the visualization component may be any visualization component known in the art. The visualization component may include, for example, one or more lenses, an eye piece, a display, a monitor, a computer, a phone, a tablet, a smart device, or any combination thereof. In certain embodiments, the visualization component may be high-definition (HD). In some embodiments, the visualization component may be coupled with the handle of the endoscope, while in other embodiments the visualization component may be separate from the endoscope. In certain embodiments, the visualization component may be wirelessly coupled to the endoscope. In some embodiments, the visualization component may be optically coupled to the scope. In other embodiments, the visualization component may be electronically coupled to the scope. In certain embodiments, the visualization may be opto-electronically coupled to the scope.

In some embodiments, at least one of the needle and the scope of the endoscope may be housed in an elongated shaft. In other embodiments, at least one of the reservoir and the dispensing mechanism may be contained within an elongated shaft. In still other embodiments, the elongated shaft may further comprise a catheter separate from the needle. In certain embodiments, the elongated shaft may further comprise a sponge applicator. In some embodiments, the sponge applicator may contain or be soaked with a composition, while in other embodiments the sponge applicator may be substantially dry. In one embodiment, the sponge applicator may be substantially saturated with a composition comprising phenol. In some embodiments, the elongated shaft may be rigid, while in other embodiments it may be flexible.

In one embodiment, at least one of the reservoir and/or the dispensing mechanism may be contained within the handle of the endoscope. In another embodiment, the reservoir and/or the dispensing mechanism may be attached externally to the endoscope. In some embodiments, the reservoir may contain a volume of the composition sufficient for multiple injections, while in other embodiments the reservoir may contain a volume of the composition sufficient for a single injection. In certain embodiments, the reservoir may have a volume from about 1 μL to about 5 mL. The reservoir may have a volume of, for example, about 1 μL, about 25 μL, about 50 μL, about 75 μL, about 100 μL, about 125 μL, about 150 μL, about 175 μL, about 200 μL, about 225 μL, about 250 μL, about 275 μL, about 300 μL, about 325 μL, about 350 μL, about 375 μL, about 400 μL, about 425 μL, about 450 μL, about 475 μL, about 500 μL, about 525 μL, about 550 μL, about 575 μL, about 600 μL, about 625 μL, about 650 μL, about 675 μL, about 700 μL, about 725 μL, about 750 μL, about 775 μL, about 800 μL, about 825 μL, about 850 μL, about 875 μL, about 900 μL, about 925 μL, about 950 μL, about 975 μL, about 1 mL, about 1.2 mL, about 1.4 mL, about 1.6 mL, about 1.8 mL, about 2 mL, about 2.2 mL, about 2.4 mL, about 2.6 mL, about 2.8 mL, about 3 mL, about 3.2 mL, about 3.4 mL, about 3.6 mL, about 3.8 mL, about 4 mL, about 4.2 mL, about 4.4 mL, about 4.6 mL, about 4.8 mL, about 5 mL, or any range between any two of these values, including endpoints.

In some embodiments, the composition may be selected from the group consisting of air, water, an anesthetic, phenol, an anti-inflammatory composition, a biologic, a protein, a peptide, a gene delivery system, a steroid, an antibiotic, a small molecule, a corticosteroid, an aminoglycoside antibiotic, dexamethasone, methylprednisolone, gentamicin, streptomycin, kanamycin, or any combination thereof. In certain embodiments, the composition may be in the form of a hydrogel, while in other embodiments the composition may be in the form of a liquid or gas. Where the composition comprises a hydrogel, the hydrogel may be non-biodegradable, biodegradable, or a combination thereof. Such hydrogels may comprise thermos-responsive poloxamer 407, hyaluronic acid, gelatin, chitosan, or combinations thereof. Such hydrogels may further comprise particulate systems, such as liposomes, polymeric nanoparticles, self-assembled polymersomes, hydrogel matrices, or combinations thereof.

In some embodiments, the at least one button of the handle may be configured to dispense the composition from the reservoir through the needle to a portion of the ear at a controlled rate. In certain embodiments, the at least one button of the handle may be configured to adjust the controlled rate. The controlled rate may be from about 0.1 mL per minute to about 30 mL per minute. The controlled rate may be, for example, about 0.1 mL per minute, about 0.25 mL per minute, about 0.5 mL per minute, about 0.75 mL per minute, about 1 mL per minute, about 2 mL per minute, about 4 mL per minute, about 6 mL per minute, about 8 mL per minute, about 10 mL per minute, about 12 mL per minute, about 14 mL per minute, about 16 mL per minute, about 18 mL per minute, about 20 mL per minute, about 22 mL per minute, about 24 mL per minute, about 26 mL per minute, about 28 mL per minute, about 30 mL per minute, or any range between any two of these values, including endpoints.

In certain embodiments, the portion of the ear to which a composition may be delivered may include any portion of the ear, or the entire ear. In embodiments, the portion of the ear may include, for example, an outer ear, a middle ear, an inner ear, an ear canal, a tympanic membrane, or any combination thereof.

In some embodiments, the at least one button, the needle, the reservoir, and the dispensing mechanism may be operably linked to cause the composition to be dispensed from the reservoir through the needle to a portion of an ear. In certain embodiments, the at least one button, the needle, the reservoir, and the dispensing mechanism may be electronically linked, while in other embodiments they may be mechanically linked, and in still other embodiments they may be electromechanically linked. In some embodiments, the dispensing mechanism may be selected from a spring-loaded mechanism, a sliding rod mechanism, a piston, an air pressurized mechanism, a pump, a peristaltic pump, a positive displacement pump, a syringe pump, a diaphragm metering pump, or any combination thereof.

In some embodiments, the endoscope may further comprise a stop component. The stop component may be configured to prevent insertion of a portion of the endoscope too far into the portion of the ear, or beyond the portion of the ear. The stop component may be coupled to the elongated shaft, or to any other component of the endoscope. In certain embodiments, the stop component may be removably coupled to an elongated shaft, while in other embodiments the stop component may be fixedly coupled to the elongated shaft. In some embodiments, the position of the stop component on the elongated shaft may be adjustable. In certain embodiments, the stop component may extend beyond an end of the endoscope and/or an end of the elongated shaft. In one embodiment, the stop component may comprise a speculum. In certain embodiments, the speculum may function as both a physical stop to prevent mistaken deep penetration of an ear, and may also be used to properly position the endoscope within the ear. The speculum may further function to stabilize the endoscope during the administration of a composition. In one embodiment, the speculum may comprise a hard plastic bell. The speculum may further comprise a soft-seal tip, and/or an outer layer of a compressible material such as a foam to conform to a portion of the ear and provide stability.

In some embodiments, the endoscope may further comprise a battery having a voltage. In an embodiment, the voltage may be from about 1V to about 15V. The voltage may be, for example, about 1V, about 2V, about 3V, about 4V, about 5V, about 6V, about 7V, about 8V, about 9V, about 10V, about 11V, about 12V, about 13V, about 14V, about 15V, or any range between any two of these values, including endpoints. In certain embodiments, the battery may be external to the endoscope and may be connected by one or more wires. In other embodiments, the battery may be housed within the endoscope.

In certain embodiments, the endoscope may further comprise at least one laser. The laser may include a straight laser, an angled laser, or any combination thereof. In one embodiment, the laser may be housed in the elongated shaft of the endoscope. In one embodiment, the straight laser may be configured to indicate a target location of in the portion of the ear. In some embodiments, the target location may be a target location for a needle puncture. In an embodiment, the angled laser may be configured to determine a distance to the portion of the ear. In an embodiment, the distance may be the distance to the tympanic membrane.

In some embodiments, the endoscope may further comprise one or more sensors. In an embodiment, the one or more sensors may be configured to detect the puncture of a portion of the ear, such as the tympanic membrane. In certain embodiments, the sensor may be selected from a miniature acoustic sensor, a microphone, a pressure sensor, a surface acoustic wave (SAW) pressure sensor, a capacitive touch sensor, a vibrational sensor, a spring-loaded pressure sensor, or any combination thereof. In one embodiment, the miniature acoustic sensor and/or microphone may be configured to detect the "pop" of a tympanic membrane as the needle punctures the tympanic membrane. In another embodiment, the sensor may be located at the needle tip and may be configured to detect the pressure change when the needle punctures the tympanic membrane (e.g., based on the modulation of SAWs). In still another embodiment, the capacitive touch sensor may be configured to detect the contact between the needle and the tympanic membrane. In other embodiments, the vibrational sensor may be configured to detect the resistance from the needle when it punctures the tympanic membrane. In still other embodiments, a spring-loaded pressure sensor may be used to detect a first pressure change (i.e., an increase) when the needle contacts the tympanic membrane, and a second pressure change (i.e., a decrease) when the tympanic membrane is punctured. In certain embodiments, the one or more sensors may be located along the needle, at the needle tip, along the elongated shaft, or any combination thereof.

Figure 2:
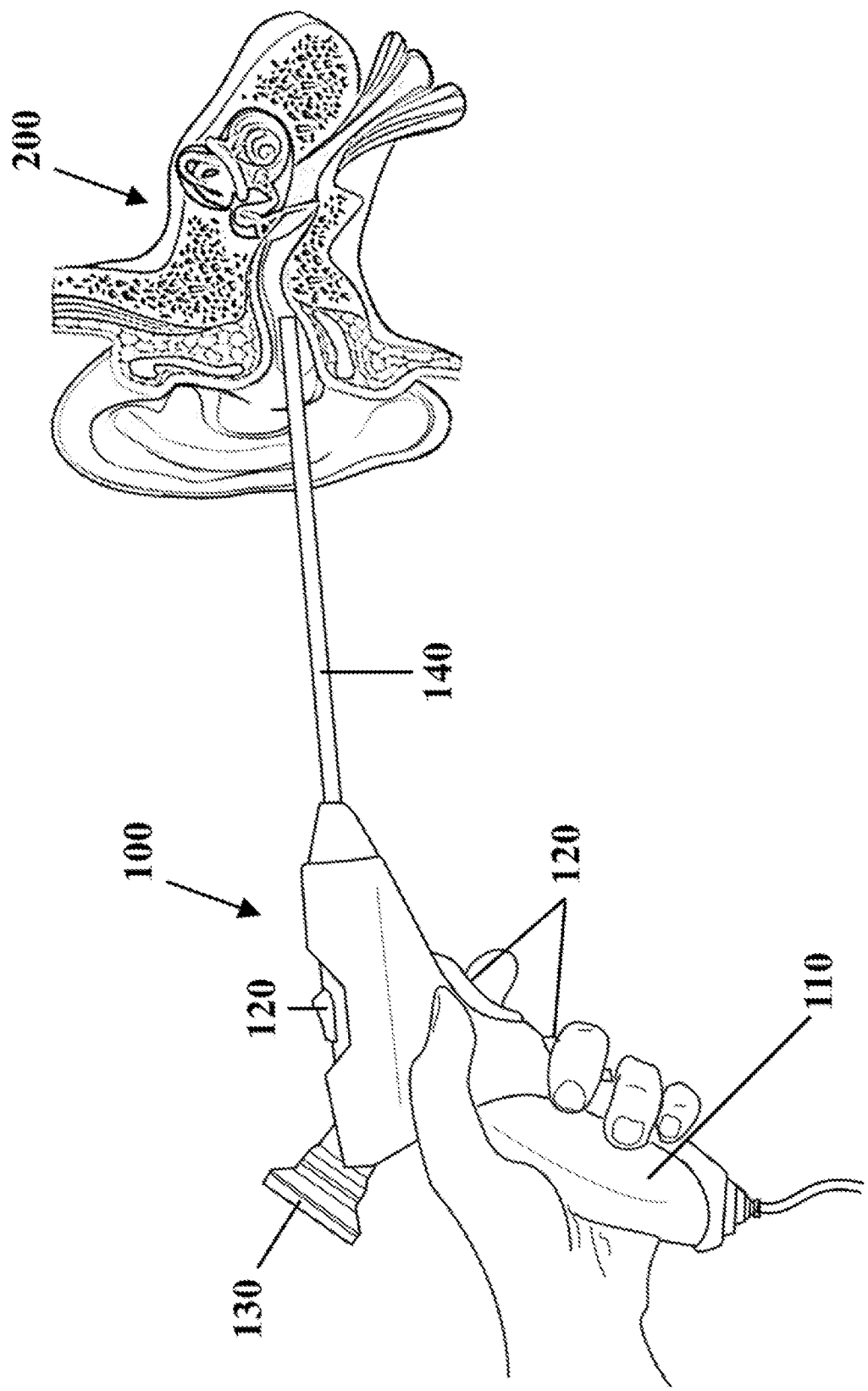
FIG. 2 illustrates an embodiment of an endoscope being inserted into a portion of an ear, in accordance with the present disclosure.

The figures included in the present disclosure illustrate various non-limiting embodiments of endoscopes as described herein. FIG. 1 illustrates an embodiment of an endoscope 100 comprising a handle 110, three buttons 120, a visualization component 130 comprising an eyepiece, and an elongated shaft 140. The three buttons 120 of FIG. 1 are configured to dispense the composition, deploy the needle, and retract the needle, respectively. FIG. 2 illustrates an embodiment of an endoscope 100, as shown in FIG. 1, with the tip of the elongated shaft 140 inserted into a portion of an ear 200.

Figure 3:
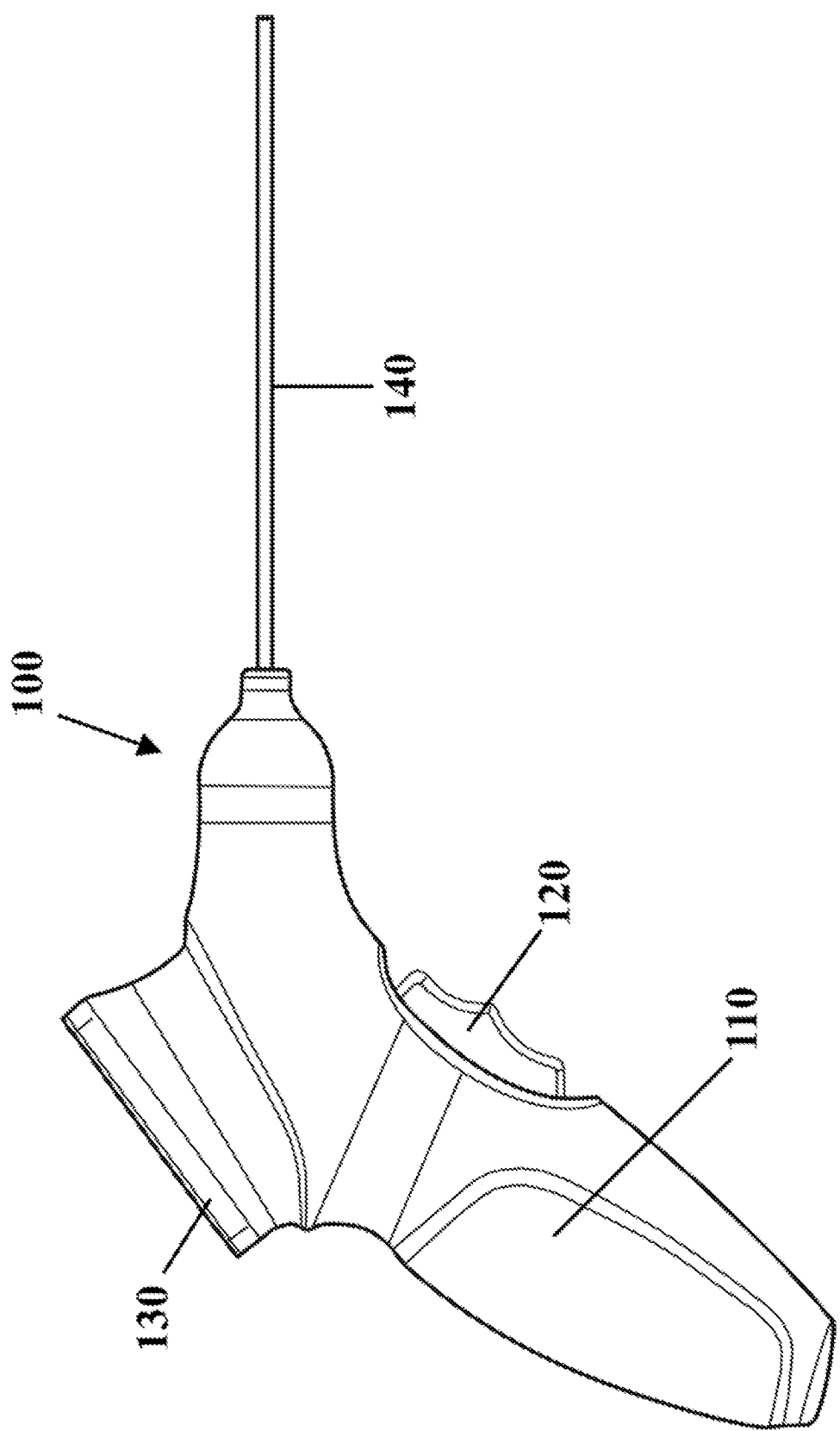
FIG. 3 illustrates an alternative embodiment of an endoscope, in accordance with the present disclosure.

FIG. 3 illustrates an alternative embodiment of an endoscope 100 comprising a handle 110, a button 120, a visualization component 130 comprising a substantially rectangular display screen, and an elongated shaft 140. The button 120 of FIG. 3 is configured to deploy and retract the needle of the endoscope.

Figure 4:
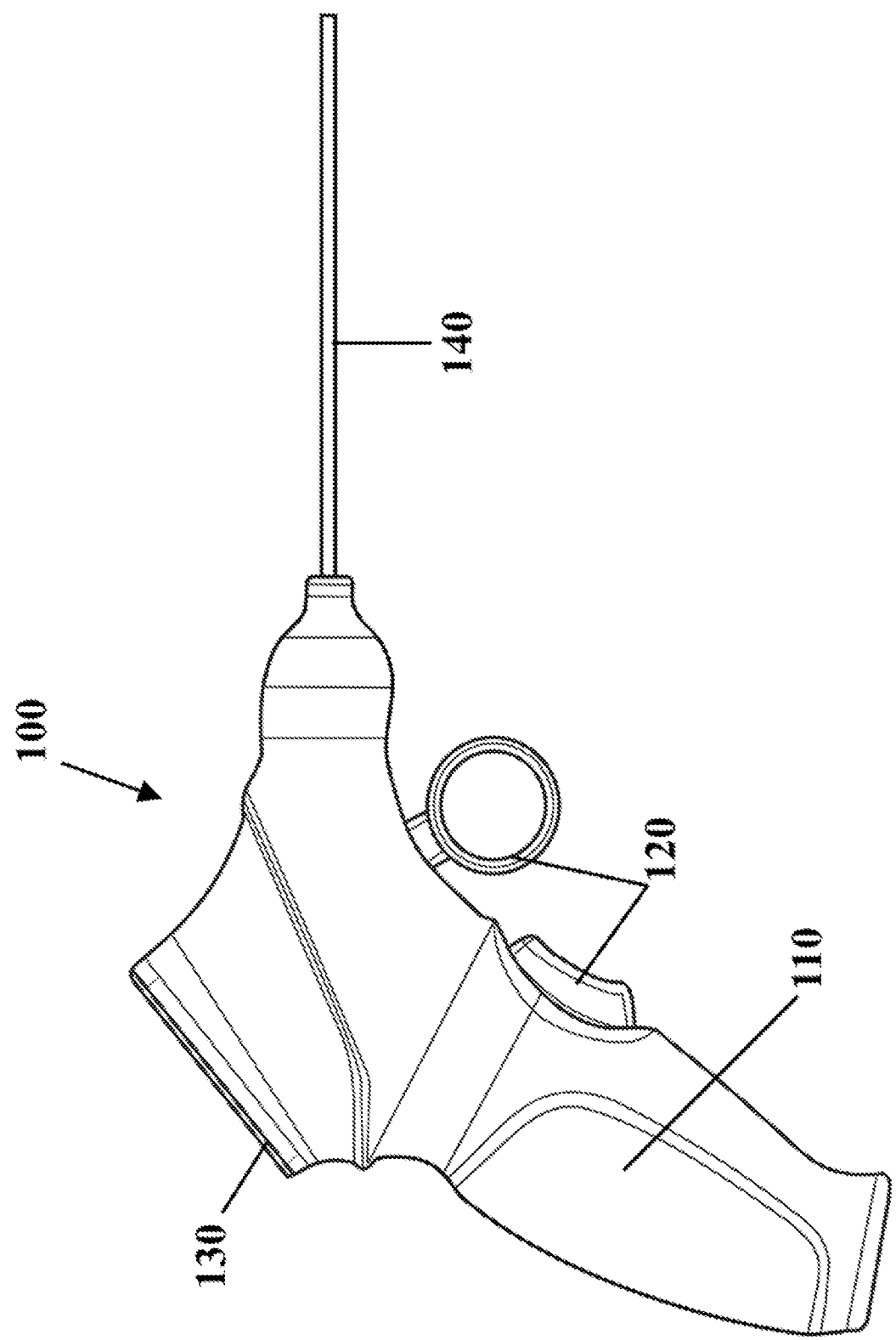
FIG. 4 illustrates an alternative embodiment of an endoscope, in accordance with the present disclosure.

FIG. 4 illustrates another alternative embodiment of an endoscope 100 comprising a handle 110, two buttons 120, a visualization component 130 comprising a substantially rectangular display screen, and an elongated shaft 140. The two buttons 120 of FIG. 4 comprise a push-button and a ring-shaped trigger. The push-button is configured to cause the composition to be dispensed, and the ring-shaped trigger is configured to advance and retract the needle of the endoscope.

Figure 5:
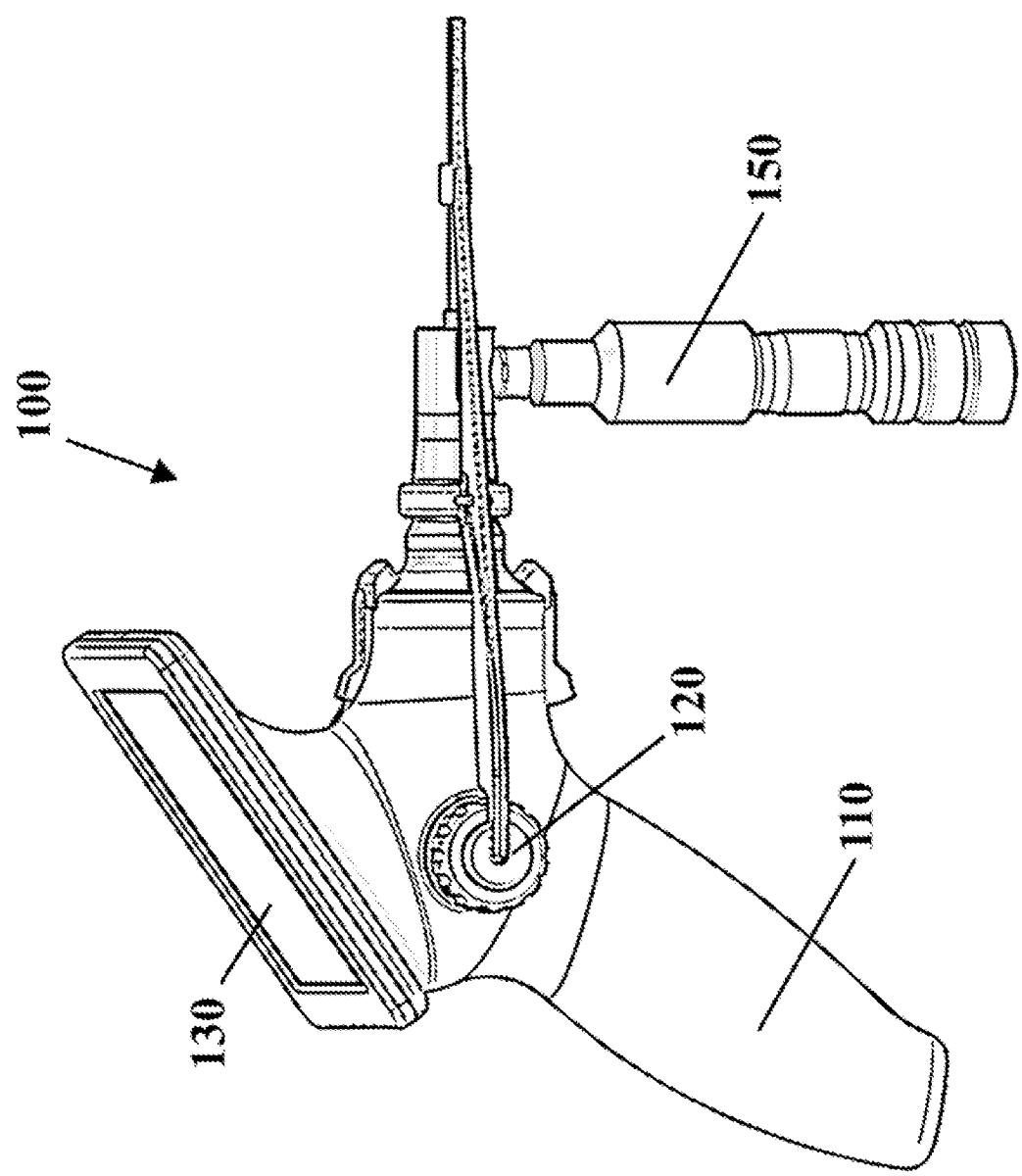
FIG. 5 illustrates an embodiment of an endoscope that includes an external battery-powered light source and is configured for use in a right ear, in accordance with the present disclosure.

FIG. 5 illustrates an alternative embodiment of an endoscope 100 comprising a handle 110, a button 120 comprising a wheel, a visualization component 130 comprising a substantially rectangular display screen, and an external battery-powered light source 150. The button 120 of FIG. 5 comprises a wheel accessible by a user's thumb, wherein the wheel is configured to advance and retract the needle of the endoscope. The endoscope 100 of FIG. 5 is configured for use in a right ear.

Figure 6A:
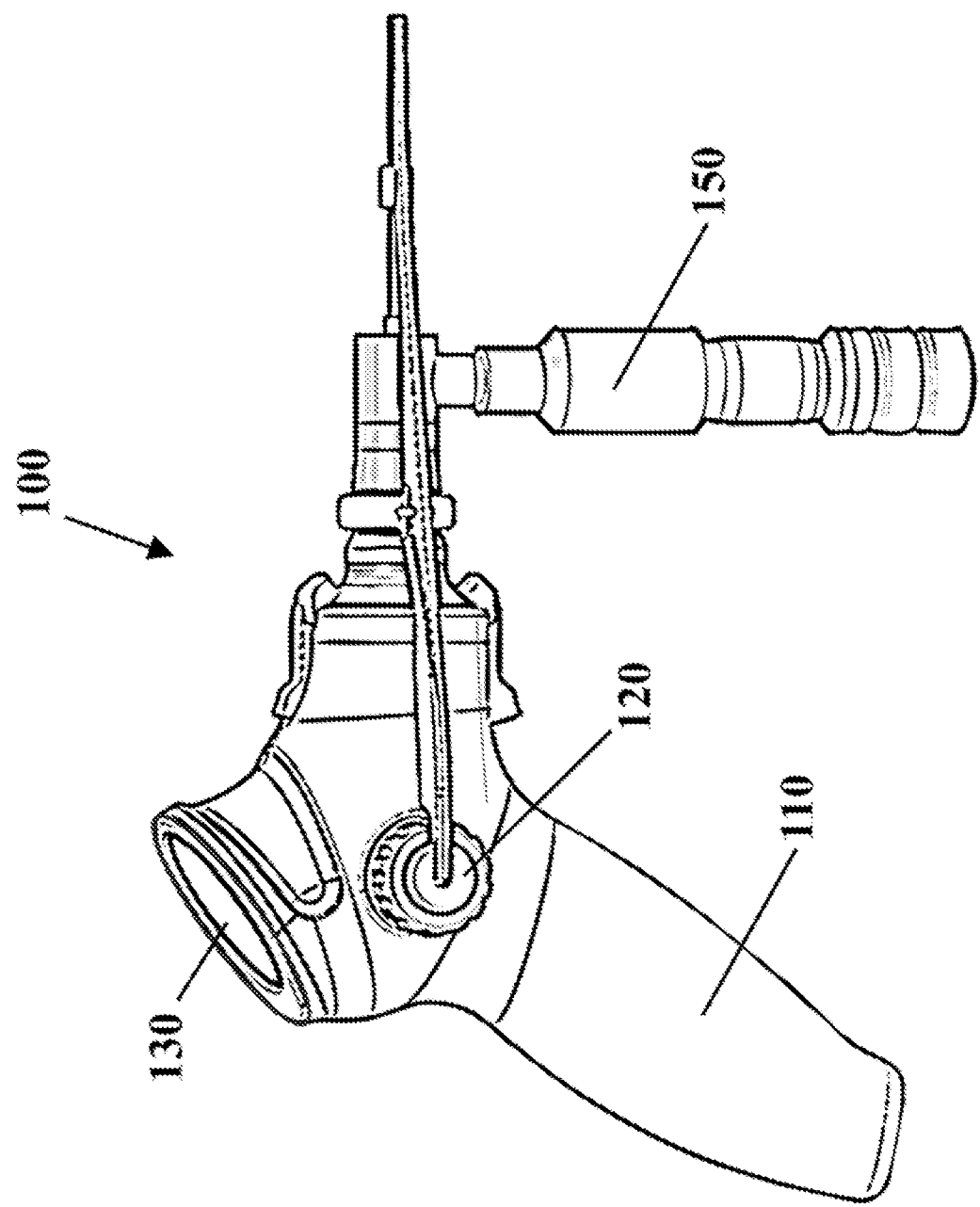
FIG. 6A illustrates an alternative embodiment of an endoscope that includes an external battery-powered light source and is configured for use in a right ear, in accordance with the present disclosure.
Figure 6B:
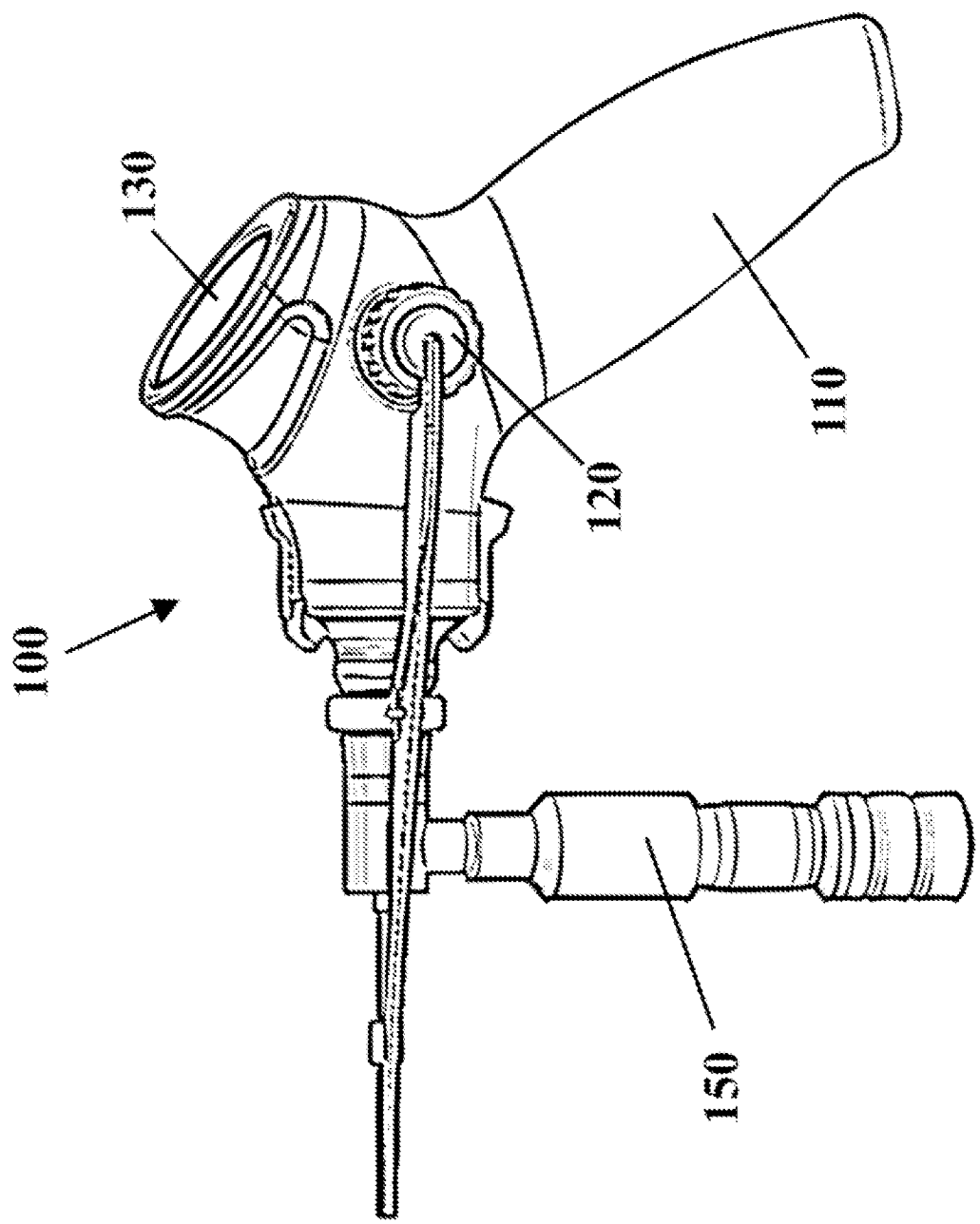
FIG. 6B illustrates an alternative embodiment of an endoscope that includes an external battery-powered light source and is configured for use in a left ear, in accordance with the present disclosure.

FIG. 6A illustrates an embodiment of an endoscope 100 similar to the embodiment shown in FIG. 5, with a handle 110, a button 120, and a light source 150 that is battery-powered, but instead having a visualization component 130 comprising a substantially circular display screen. The endoscope 100 of FIG. 6A is configured for use in a right ear, wherein the needle is housed on the right side of the endoscope. The endoscope 100 of FIG. 6B, on the other hand, is configured for use in a left ear, because the needle is housed on the left side of the endoscope.

Figure 7A:
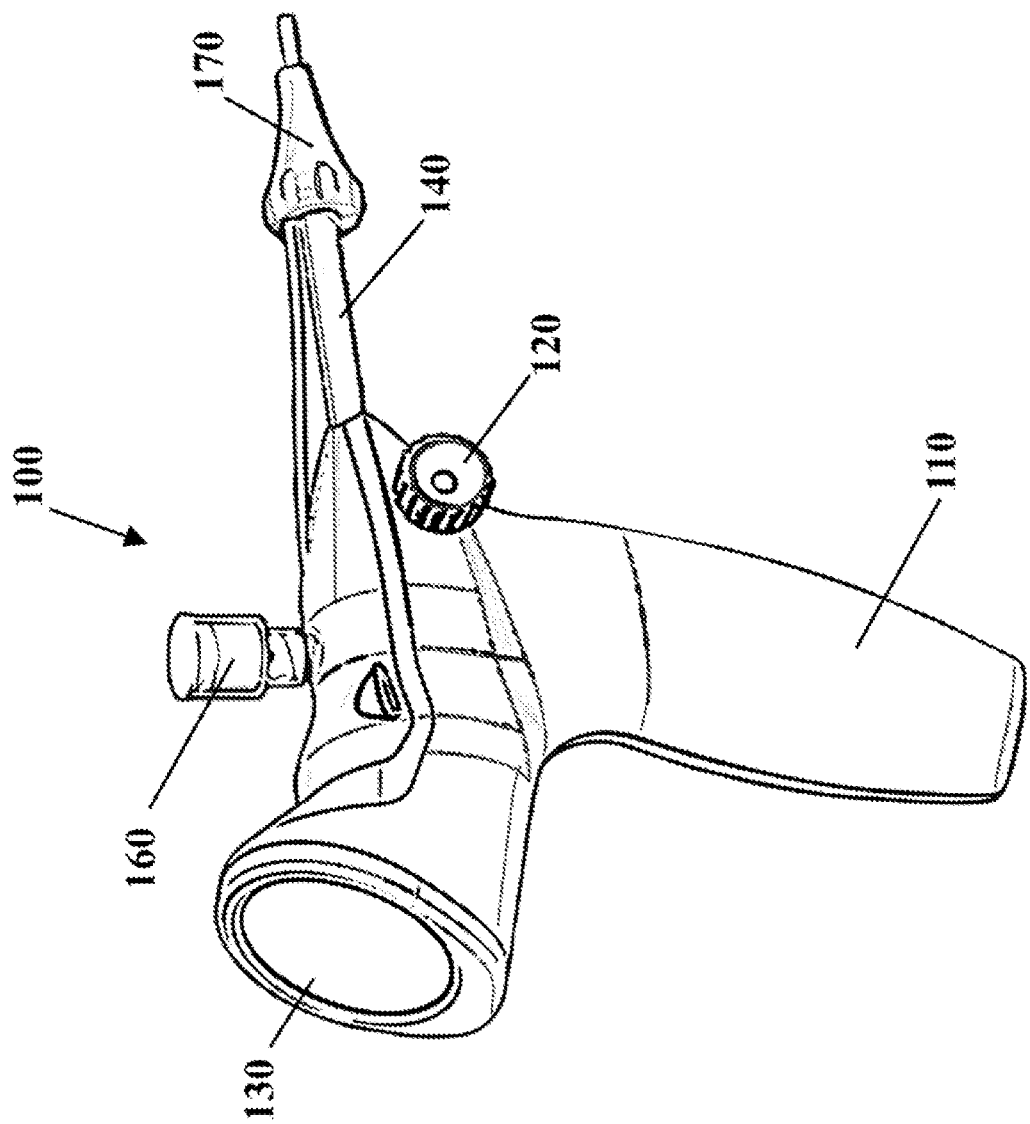
FIG. 7A illustrates an alternative embodiment of an endoscope that includes a stop component, in accordance with the present disclosure.
Figure 8:
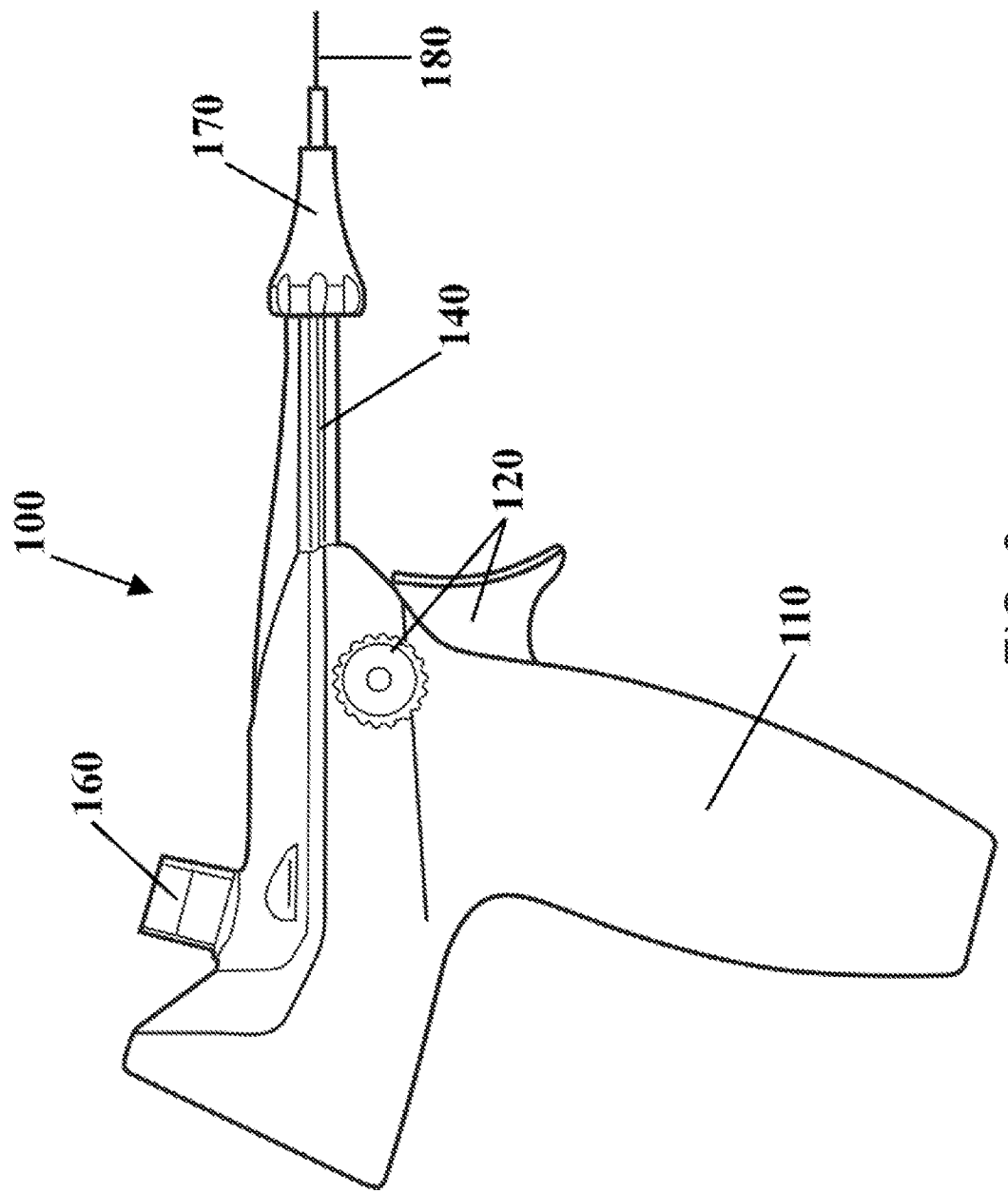
FIG. 8 illustrates an alternative embodiment of an endoscope that includes a stop component and has its needle deployed, in accordance with the present disclosure.

FIG. 7A illustrates an embodiment of an endoscope 100 comprising a handle 110, a button 120 comprising a wheel (with a second button comprising a wheel on the opposite side, not shown), a visualization component 130 comprising a substantially circular display screen, an elongated shaft 140, a reservoir 160, and a stop component 170 comprising a speculum. The buttons 120 of FIG. 7A comprise thumb wheels configured to advance and retract the needle. The endoscope 100 of FIG. 7A may also comprise a light source and/or a battery (not shown) housed within the handle 110. FIG. 7B illustrates a top view of the endoscope 100 of FIG. 7A. FIG. 7B particularly shows a button 120 on each side of the endoscope 100, along with the other components shown in FIG. 7A. The buttons 120 of FIG. 7B comprise thumb wheels that are connected, such that a user may move either thumb wheel to advance and retract the needle. FIG. 8 illustrates another embodiment of an endoscope 100 comprising a handle 110, two buttons 120, an elongated shaft 140, a reservoir 160, a stop component 170 comprising a speculum, and a deployed needle 180.

Figure 9:
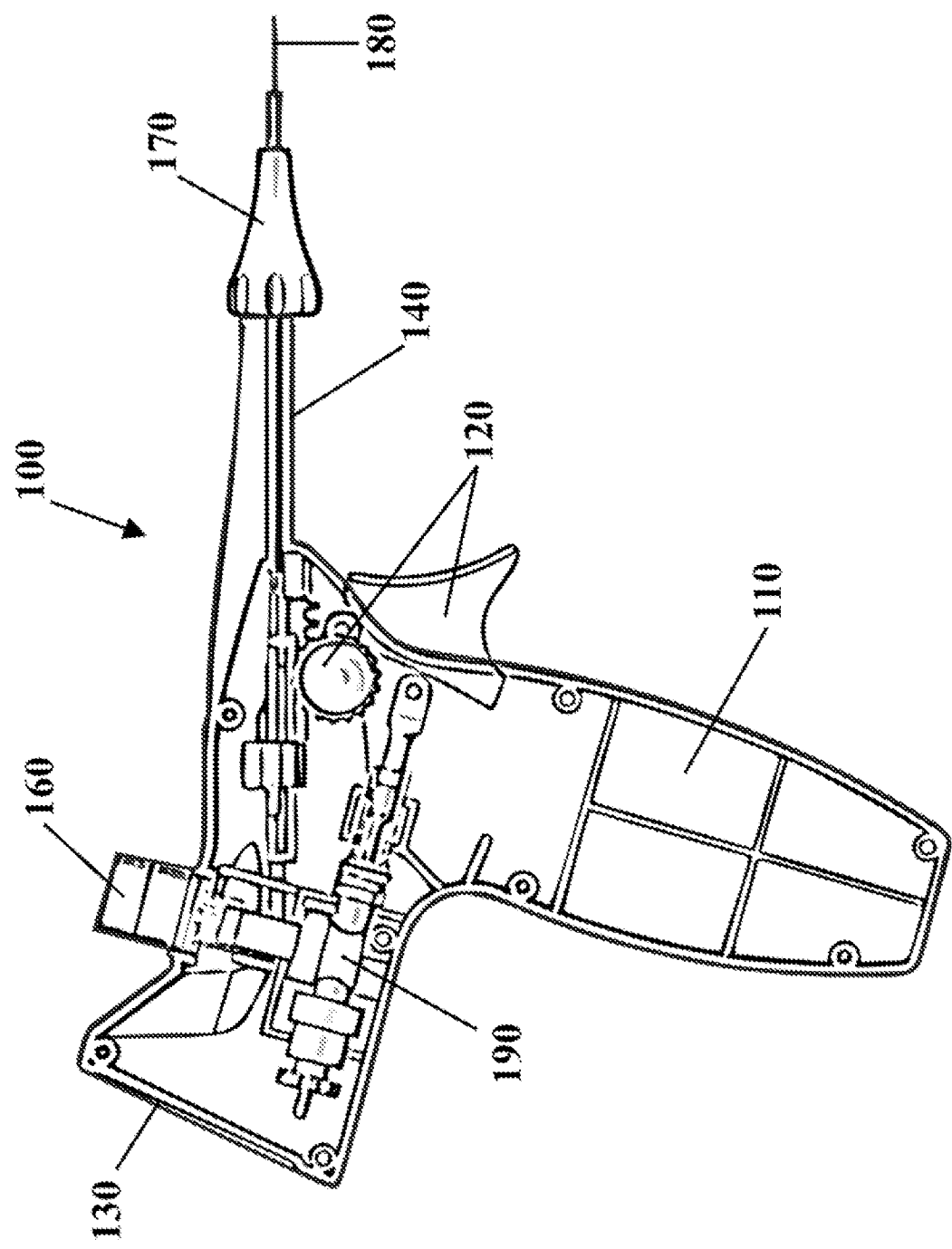
FIG. 9 illustrates a cross-sectional view of an embodiment of an endoscope, in accordance with the present disclosure.

FIG. 9 illustrates a cross-sectional view of an embodiment of an endoscope 100, comprising a handle 110, two buttons 120, a visualization component 130, an elongated shaft 140, a reservoir 160, a stop component 170 comprising a speculum, a deployed needle 180, and a dispensing mechanism 190. The dispensing mechanism 190 of the endoscope 100 of FIG. 9 comprises a pump configured to dispense the composition from the reservoir 160 by pressing the button 120 that comprises a trigger. The dispensing mechanism 190 of the endoscope 100 of FIG. 9 further comprises a rack and pinion configuration configured to advance and retract the needle 180 by pressing the button 120 that comprises a thumb wheel.

Figure 10:
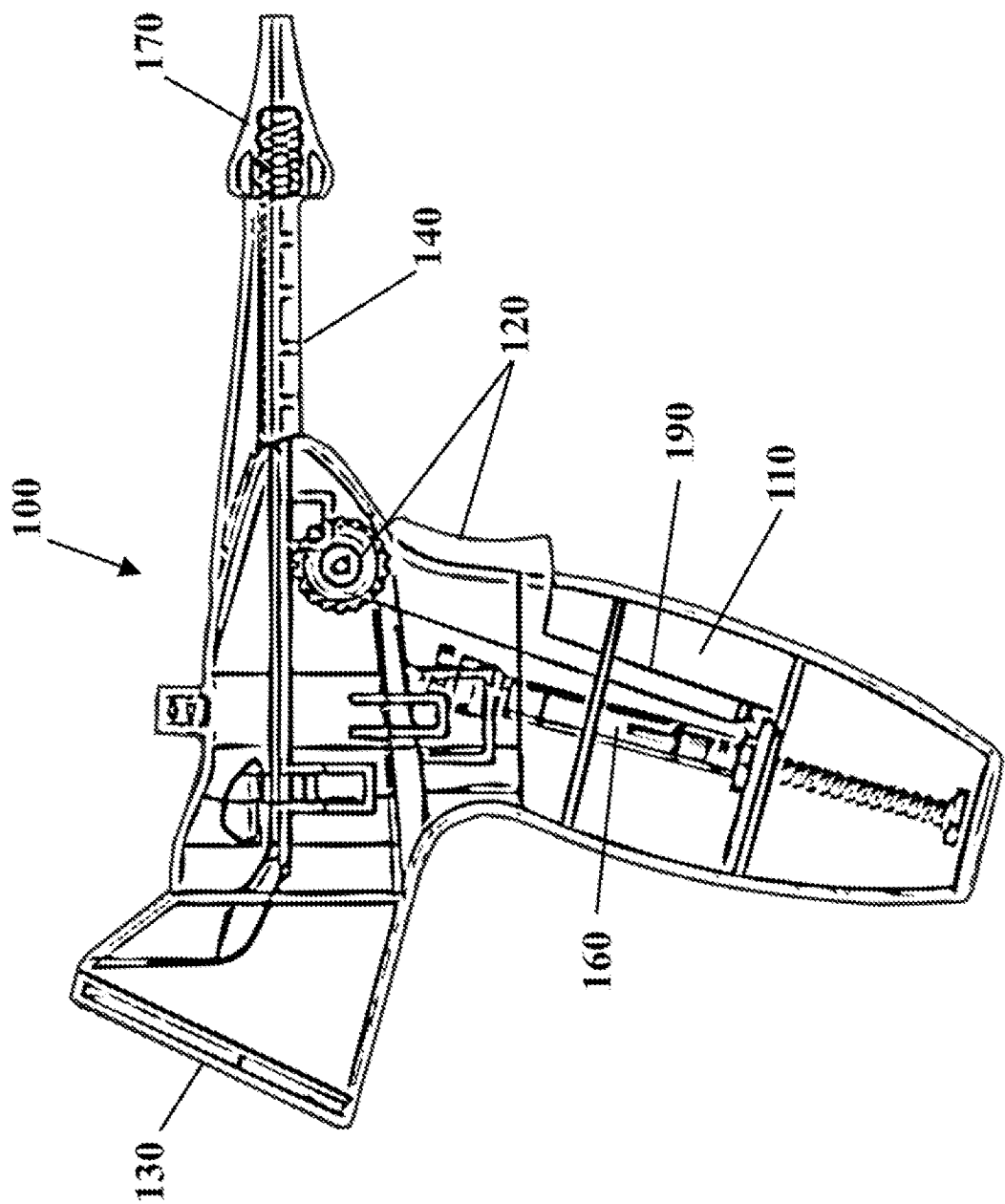
FIG. 10 illustrates a cross-sectional view of an alternative embodiment of an endoscope, in accordance with the present disclosure.

FIG. 10 illustrates a cross-sectional view of another embodiment of an endoscope 100, comprising a handle 110, two buttons 120, a visualization component 130, an elongated shaft 140, a reservoir 160, a stop component 170 comprising a speculum, a needle (not shown), and a dispensing mechanism 190. The dispensing mechanism 190 of the endoscope 100 of FIG. 10 comprises a racket arm configured to advance a racket pin to mechanically dispense the composition from the reservoir 160 by pressing the button 120 that comprises a trigger. The button 120 that comprises a trigger is connected to the racket arm and is configured to dispense the composition.

Figure 11:
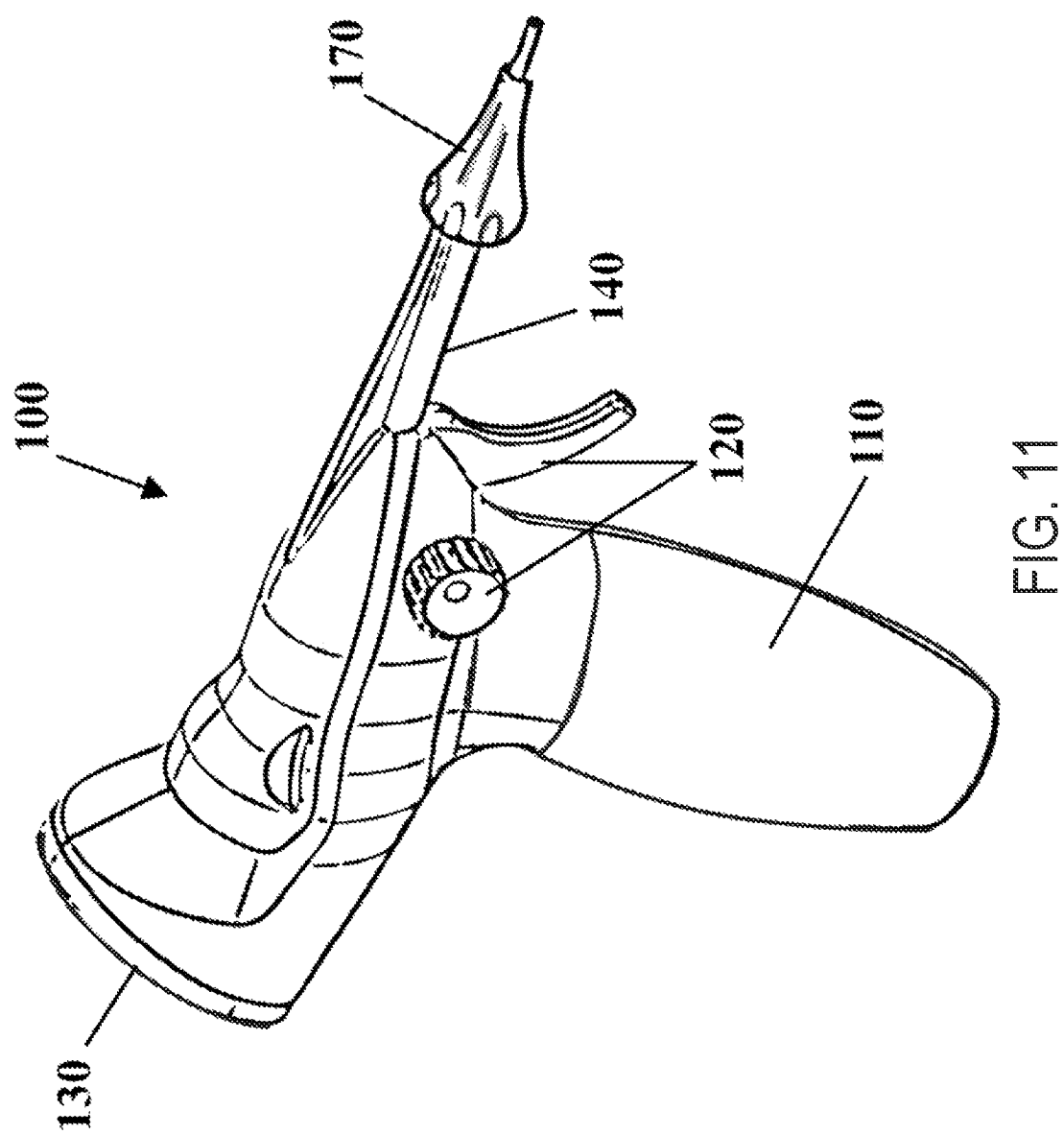
FIG. 11 illustrates an alternative embodiment of an endoscope that includes a stop component, in accordance with the present disclosure.

FIG. 11 illustrates an embodiment of an endoscope 100 comprising a handle 110, two buttons 120, a visualization component 130 comprising a substantially circular display screen, an elongated shaft 140, and a stop component 170 comprising a speculum. The endoscope 100 of FIG. 11 may also comprise a reservoir (not shown) housed within the endoscope 100, and the button 120 of FIG. 11 that comprises a trigger may be configured to dispense the composition from the reservoir.

Figure 12B:
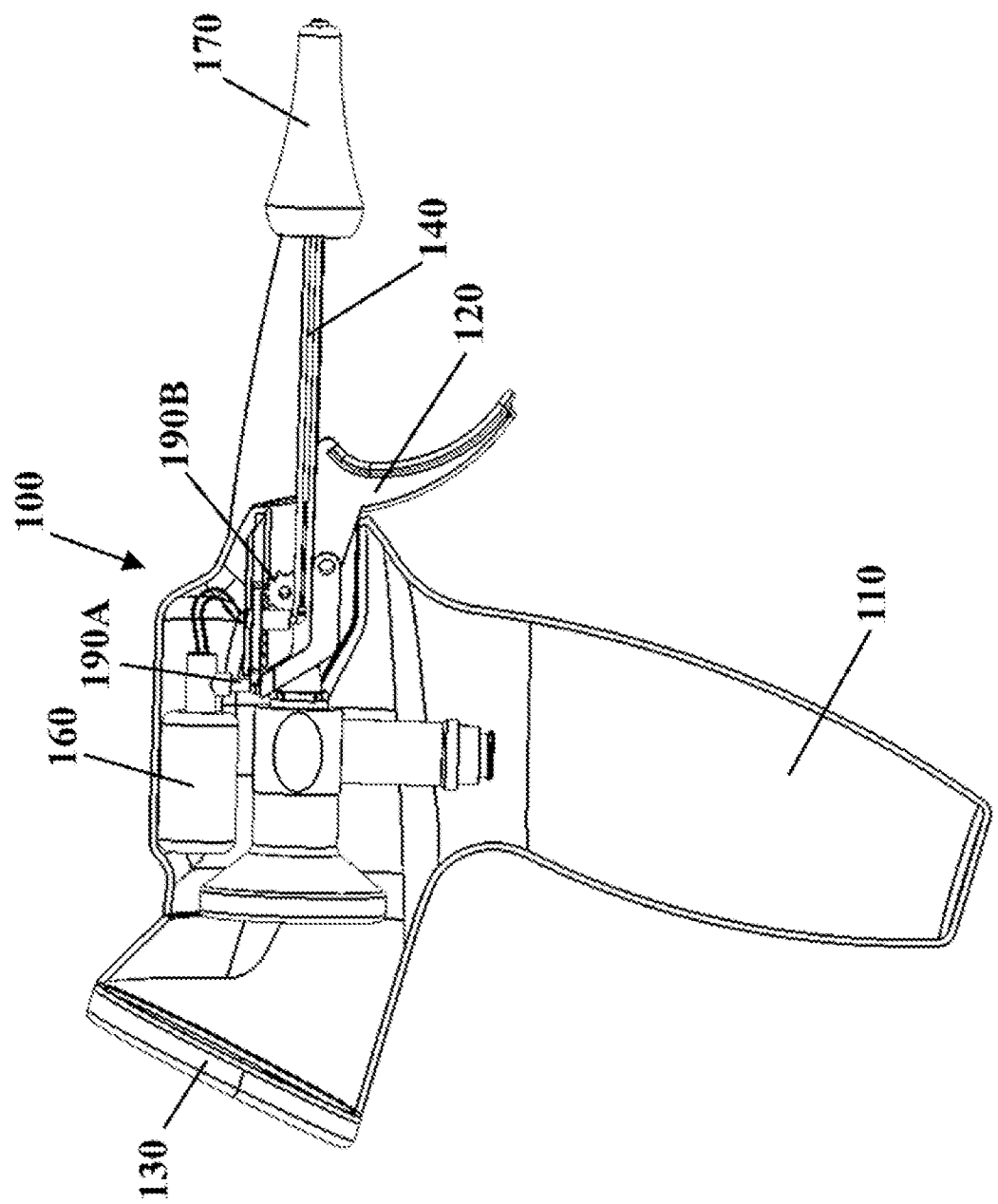
FIG. 12B illustrates a cross-sectional view of the endoscope of FIG. 12A, in accordance with the present disclosure.
Figure 12C:
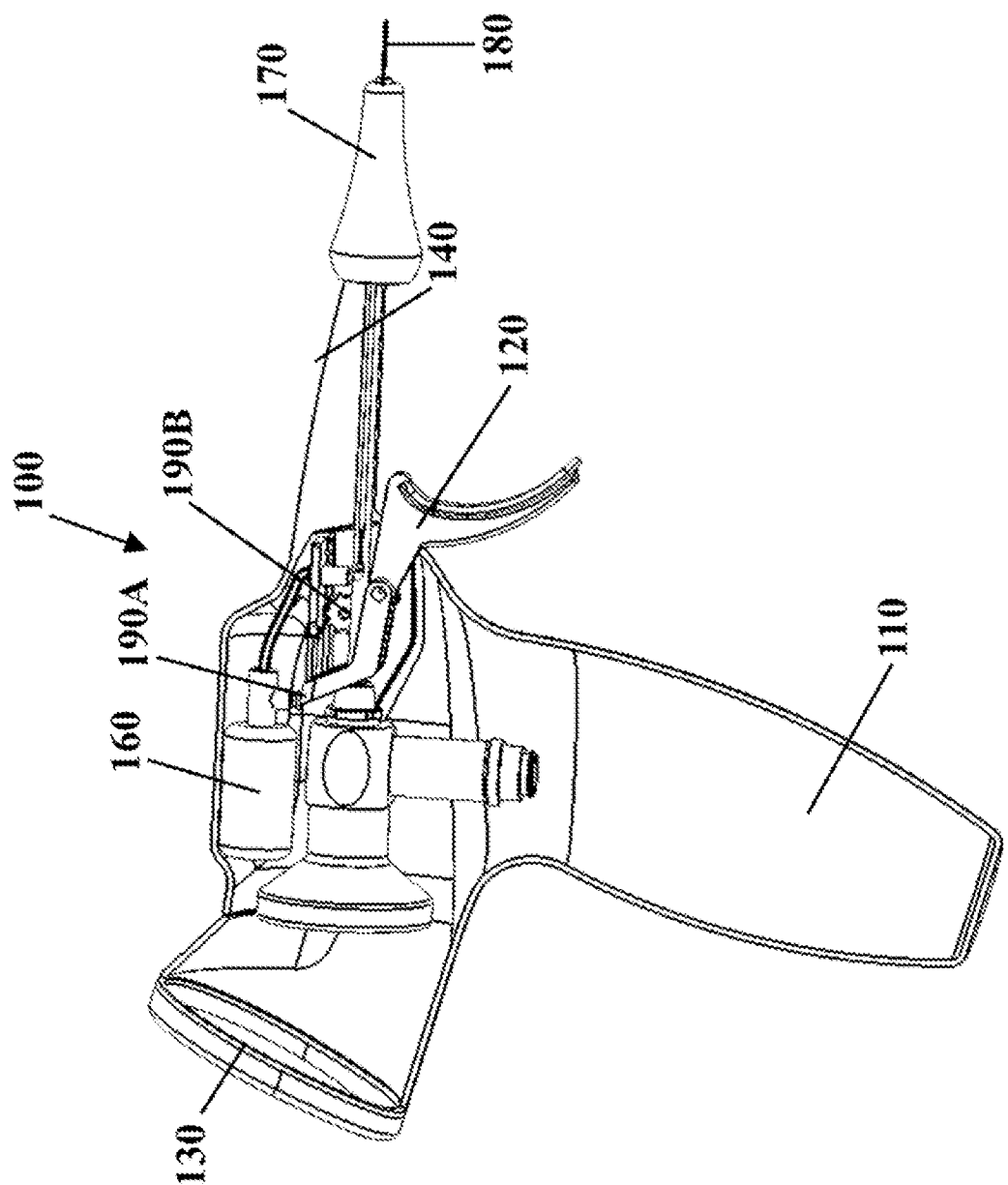
FIG. 12C illustrates a cross-sectional view of the endoscope of FIG. 12A with its needle deployed, in accordance with the present disclosure.

FIG. 12A illustrates an embodiment of an endoscope 100 comprising a handle 110, two buttons 120, a visualization component 130 comprising a substantially circular display screen, an elongated shaft 140, and a stop component 170. The endoscope 100 of FIG. 12A may also comprise a reservoir (not shown) housed within the endoscope 100, and the button 120 of FIG. 12A that comprises a trigger may be configured to dispense the composition from the reservoir. FIG. 12B illustrates a cross-sectional view of the endoscope 100 of FIG. 12A, in which the needle (not shown) is retracted. FIG. 12B particularly illustrates the location of the reservoir 160 within the endoscope 100. FIG. 12B also illustrates the dispensing mechanism 190A and 190B of the endoscope 100. The dispensing mechanism 190A and 190B of the endoscope 100 of FIG. 12B comprises a flexible tubing connecting the reservoir 160 to a rack and pinion mechanism (190B) for advancing and retracting the needle (not shown), and the button 120 of FIG. 12B that comprises a trigger has a lever arm that is mechanically configured to dispense the composition from the reservoir 160. FIG. 12C illustrates the cross-sectional view of the endoscope 100 of FIG. 12B, but in an alternate configuration in which the needle 180 is deployed, which has modified the position of the rack and pinion mechanism and consequently straightened the flexible tubing connecting the reservoir 160 to the rack and pinion mechanism.

Figure 13:
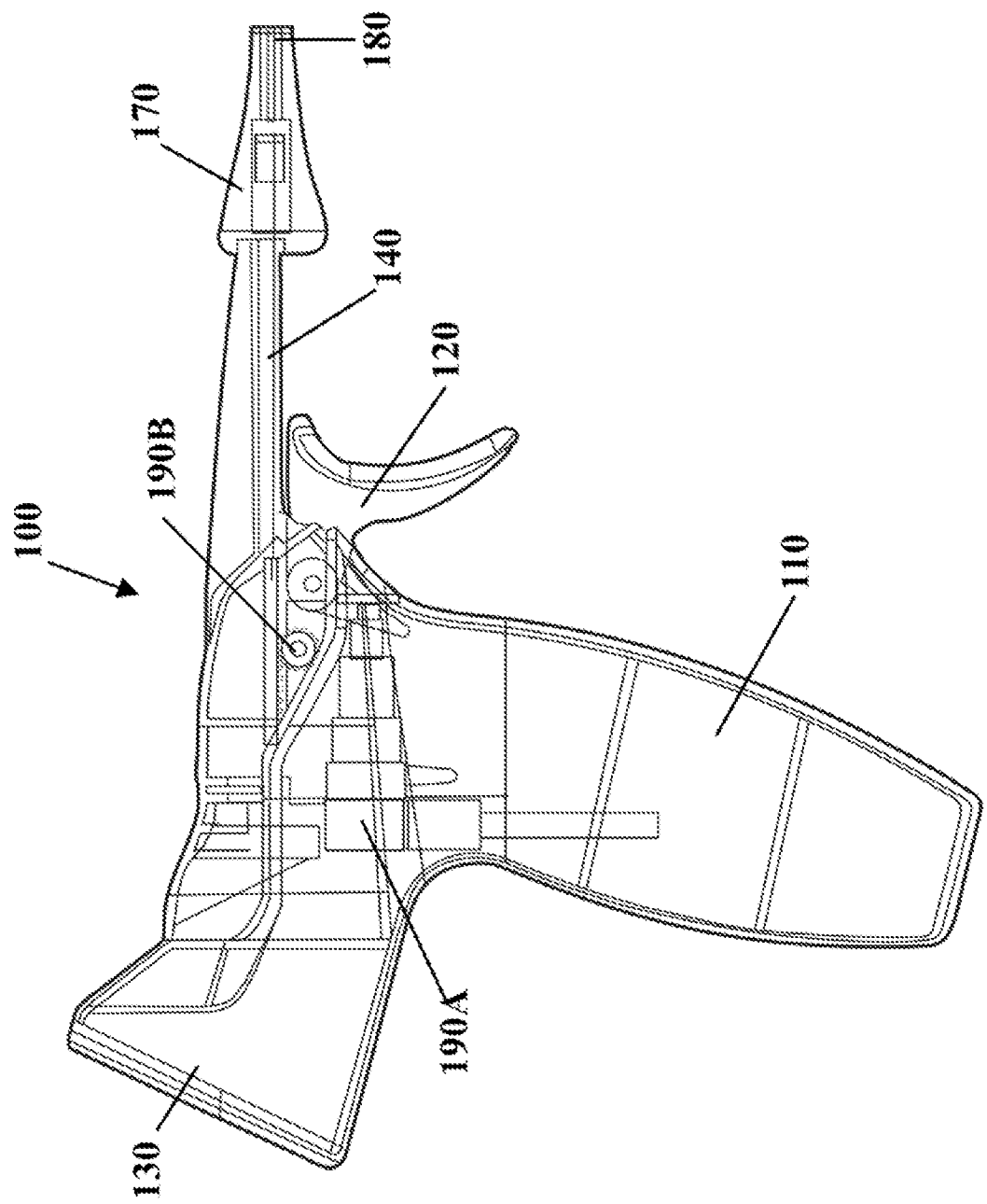
FIG. 13 illustrates a cross-sectional view of an alternative embodiment of an endoscope, in accordance with the present disclosure.

FIG. 13 illustrates a cross-sectional view of an alternative embodiment of an endoscope 100 comprising a handle 110, a button 120, a visualization component 130, an elongated shaft 140 housing a needle 180, a stop component 170, and a dispensing mechanism 190A and 190B. The dispensing mechanism 190A of the endoscope 100 of FIG. 13 comprises a pump for dispensing the composition, and the dispensing mechanism 190B of the endoscope 100 of FIG. 13 comprises a rack and pinion mechanism configured to advance and retract the needle 180.

Various methods of using an endoscope as described herein are contemplated. In an embodiment, a method for using such an endoscope may include inserting the endoscope into a portion of an ear, using the visualization component to visualize the portion of the ear, and pressing the at least one button to dispense the composition from the reservoir through the needle to the portion of the ear. In certain embodiments, the at least one button may comprise a first button and a second button. In one embodiment, the first button is a wheel configured to facilitate advancing the needle and retracting the needle, and wherein the second button is a trigger configured to dispense the composition.

Such methods may include repeating one or more of the steps described herein. For example, in one embodiment, a method for using an endoscope may comprise inserting into a portion of an ear an endoscope as described herein, using the visualizing component to visualize the portion of the ear, and optionally, pressing the at least one button to dispense a topical anesthetic from the reservoir through the needle to the portion of the ear (such as a tympanic membrane). In alternative embodiments, the topical anesthetic may optionally be applied using a separate applicator, while in still other embodiments the topical anesthetic may not be applied at all. Once the optional topical anesthetic has reached the portion of the ear (such as the tympanic membrane), the method may further comprise advancing a portion of the endoscope (such as the needle) through the portion of the ear (such as the tympanic membrane), monitoring the advancement of the portion of the endoscope (such as the needle) through the portion of the ear (such as the tympanic membrane) through the visualization component and/or one or more sensors incorporated into the endoscope, and pressing the at least one button to dispense a second composition into a portion of the ear (such as the middle ear). Once the second composition has reached the portion of the ear (such as the middle ear), the needle may be retracted, and the endoscope may be removed from the ear.

In an embodiment, an endoscope comprises: a needle and a scope; a handle comprising at least one button; a visualization component; a reservoir configured to contain a composition; and a dispensing mechanism; wherein the at least one button, the needle, the reservoir, and the dispensing mechanism are operably linked to cause the composition to be dispensed from the reservoir through the needle to a portion of an ear. The needle and the scope may be housed in an elongated shaft. The needle may be selected from the group consisting of a sharp needle, a beveled needle, a blunt needle, a catheter, and combinations thereof. The scope may comprise at least one lens and a fiber optic light transmission component. The reservoir and the dispensing mechanism may be contained within an elongated shaft. The reservoir and the dispensing mechanism may be contained within the handle. The reservoir may be attached to an external surface of the handle. The at least one button, the needle, the reservoir, and the dispensing mechanism may be electronically linked. The at least one button, the needle, the reservoir, and the dispensing mechanism may be mechanically linked. The at least one button, the needle, the reservoir, and the dispensing mechanism may be electromechanically linked. The at least one button may facilitate a function selected from the group consisting of advancing the needle, retracting the needle, dispensing the composition, and combinations thereof. The at least one button may be selected from the group consisting of a push-button, a wheel, a trigger, and combinations thereof. The at least one button may comprise a first button and a second button, and the first button and the second button may be independently selected from the group consisting of a push-button, a wheel, a trigger, and combinations thereof. The first button may be a wheel configured to facilitate advancing the needle and retracting the needle, and the second button may be a trigger configured to dispense the composition. The elongated shaft may be rigid. The elongated shaft may be flexible. The scope may comprise a component selected from the group consisting of a fiber optic cable, a digital imaging chip, and a sensor. The scope may be selected from the group consisting of a flexible scope and a rigid scope. The scope may be selected from the group consisting of an optical scope and a digital scope. The elongated shaft may further comprise a catheter. The needle may be configured to be selectively deployed and retracted by pressing the at least one button of the handle. The needle may be detachable and disposable. The handle may further comprise a camera. The camera may be a high-definition camera. The camera may be coupled to the visualization component. The handle may further comprise a light source. The light source may be an LED light. The light source may be battery-powered. The endoscope may further comprise a stop component. The stop component may be removably coupled to an elongated shaft. The visualization component may be selected from the group consisting of a lens, an eye piece, a display, a monitor, a computer, a phone, a tablet, a smart device, and combinations thereof. The dispensing mechanism may be selected from the group consisting of a spring-loaded mechanism, a sliding rod mechanism, a piston, an air pressurized mechanism, a pump, a peristaltic pump, a positive displacement pump, a syringe pump, a diaphragm metering pump, and combinations thereof. The at least one button of the handle may be configured to dispense the composition from the reservoir through the needle to the portion of the ear at a controlled rate, and the at least one button of the handle may be configured to adjust the controlled rate. The controlled rate may be about from about 0.1 mL per minute to about 30 mL per minute. The reservoir may have a volume of about 1 µL to about 5 mL. The composition may be selected from the group consisting of air, water, an anesthetic, phenol, an anti-inflammatory composition, a biologic, a protein, a peptide, a gene delivery system, a steroid, an antibiotic, a small molecule, and combinations thereof. The portion of the ear may be selected from the group consisting of an outer ear, a middle ear, an inner ear, an ear canal, a tympanic membrane, and combinations thereof. The endoscope may further comprise a battery having a voltage from about 1V to about 15V. The elongated shaft may further comprise a sponge applicator. The endoscope may further comprise a straight laser configured to indicate a target location in the portion of the ear. The endoscope of may further comprise an angled laser configured to determine a distance to the portion of the ear. The needle may comprise a colored band configured to act as a bevel indicator. The endoscope may further comprise a sensor configured to detect the puncture of the portion of the ear. The sensor may be selected from the group consisting of a miniature acoustic sensor, a microphone, a pressure sensor, a surface acoustic wave pressure sensor, a capacitive touch sensor, a vibrational sensor, a spring-loaded pressure sensor, and combinations thereof.

The sensor may be placed in a location selected from the group consisting of along the needle, at the needle tip, and along the elongated shaft.

In an embodiment, a method for using an endoscope comprises: inserting into a portion of an ear an endoscope comprising: a needle and a scope; a handle comprising at least one button and a visualization component; a reservoir configured to contain a composition; and a dispensing mechanism; wherein the at least one button, the needle, the reservoir, and the dispensing mechanism are operably linked to cause the composition to be dispensed from the reservoir through the needle to the portion of the ear; using the visualization component to visualize the portion of the ear; and pressing the at least one button to dispense the composition from the reservoir through the needle to the portion of the ear. The needle and the scope may be housed in an elongated shaft. The needle may be selected from the group consisting of a sharp needle, a beveled needle, a blunt needle, a catheter, and combinations thereof. The scope may comprise at least one lens and a fiber optic light transmission component. The reservoir and the dispensing mechanism may be contained within an elongated shaft. The reservoir and the dispensing mechanism may be contained within the handle. The reservoir may be attached to an external surface of the handle. The at least one button, the needle, the reservoir, and the dispensing mechanism may be electronically linked. The at least one button, the needle, the reservoir, and the dispensing mechanism may be mechanically linked. The at least one button, the needle, the reservoir, and the dispensing mechanism may be electromechanically linked. The at least one button may facilitate a function selected from the group consisting of advancing the needle, retracting the needle, dispensing the composition, and combinations thereof. The at least one button may be selected from the group consisting of a push-button, a wheel, a trigger, and combinations thereof. The at least one button may comprise a first button and a second button, and the first button and the second button may be independently selected from the group consisting of a push-button, a wheel, a trigger, and combinations thereof. The first button may be a wheel configured to facilitate advancing the needle and retracting the needle, and the second button may be a trigger configured to dispense the composition. The elongated shaft may be rigid. The elongated shaft may be flexible. The scope may comprise a component selected from the group consisting of a fiber optic cable, a digital imaging chip, and a sensor. The scope may be selected from the group consisting of a flexible scope and a rigid scope. The scope may be selected from the group consisting of an optical scope and a digital scope. The elongated shaft may further comprise a catheter. The needle may be configured to be selectively deployed and retracted by pressing the at least one button of the handle. The needle may be detachable and disposable. The handle may further comprise a camera. The camera may be a high-definition camera. The camera may be coupled to the visualization component. The handle may further comprise a light source. The light source may be an LED light. The light source may be battery-powered. The endoscope may further comprise a stop component. The stop component may be removably coupled to an elongated shaft. The stop component may be configured to mechanically prevent the insertion of the rigid endoscope beyond the portion of the ear. The visualization component may be selected from the group consisting of a lens, an eye piece, a display, a monitor, a computer, a phone, a tablet, a smart device, and combinations thereof. The dispensing mechanism may be selected from the group consisting of a spring-loaded mechanism, a sliding rod mechanism, a piston, an air pressurized mechanism, a pump, a peristaltic pump, a positive displacement pump, a syringe pump, a diaphragm metering pump, and combinations thereof. The at least one button of the handle may be configured to dispense the composition from the reservoir through the needle to the portion of the ear at a controlled rate, and the at least one button of the handle may be configured to adjust the controlled rate. The controlled rate may be about from about 0.1 mL per minute to about 30 mL per minute. The reservoir may have a volume of about 1 µL to about 5 mL. The composition may be selected from the group consisting of air, water, an anesthetic, phenol, an anti-inflammatory composition, a biologic, a protein, a peptide, a gene delivery system, a steroid, an antibiotic, a small molecule, and combinations thereof. The portion of the ear may be selected from the group consisting of an outer ear, a middle ear, an inner ear, an ear canal, a tympanic membrane, and combinations thereof. The endoscope may further comprise a battery having a voltage from about 1V to about 15V. The elongated shaft may further comprise a sponge applicator. The sponge applicator may be substantially saturated with a composition comprising phenol. The endoscope may further comprise a straight laser configured to indicate a target location in the portion of the ear. The endoscope of may further comprise an angled laser configured to determine a distance to the portion of the ear. The needle may comprise a colored band configured to act as a bevel indicator, and the method may further comprise visualizing the colored band passing through the portion of the ear. The endoscope may further comprise a sensor configured to detect the puncture of the portion of the ear. The sensor may be selected from the group consisting of a miniature acoustic sensor, a microphone, a pressure sensor, a surface acoustic wave pressure sensor, a capacitive touch sensor, a vibrational sensor, a spring-loaded pressure sensor, and combinations thereof. The sensor may be placed in a location selected from the group consisting of along the needle, at the needle tip, and along the elongated shaft.

EXAMPLES

Example 1

Figure 14A:
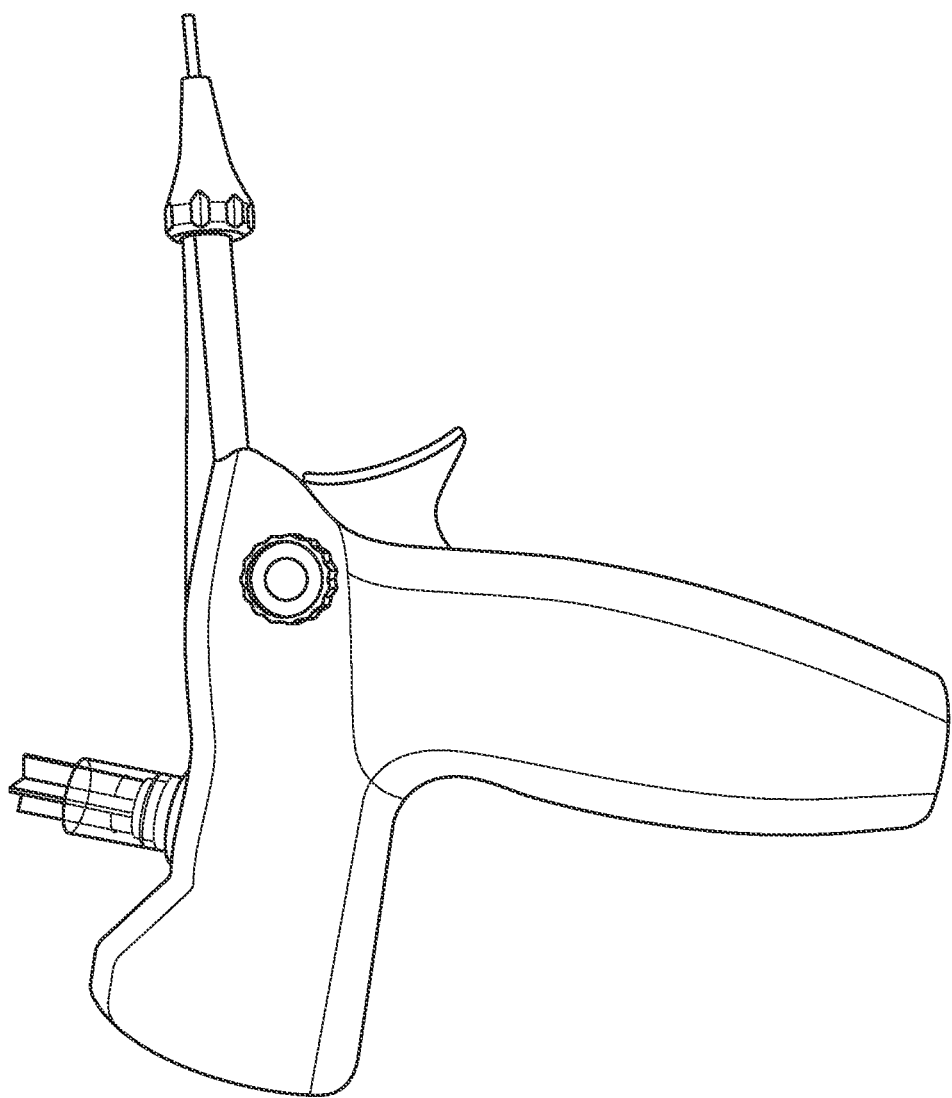
FIG. 14A shows an embodiment of a prototype of an endoscope with its needle retracted, in accordance with the present disclosure.
Figure 14B:
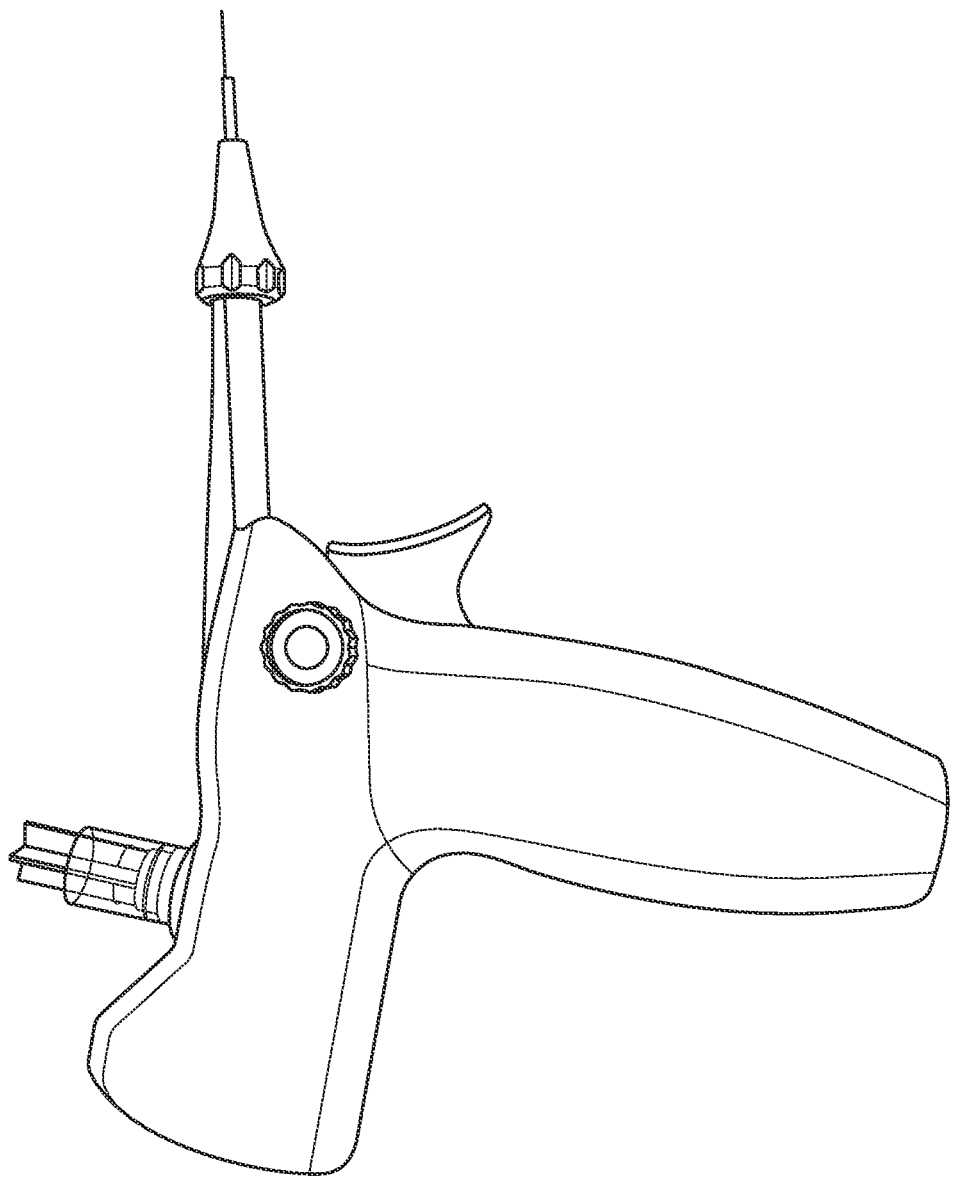
FIG. 14B shows the prototype of FIG. 14A with its needle deployed, in accordance with the present disclosure.
Figure 15:
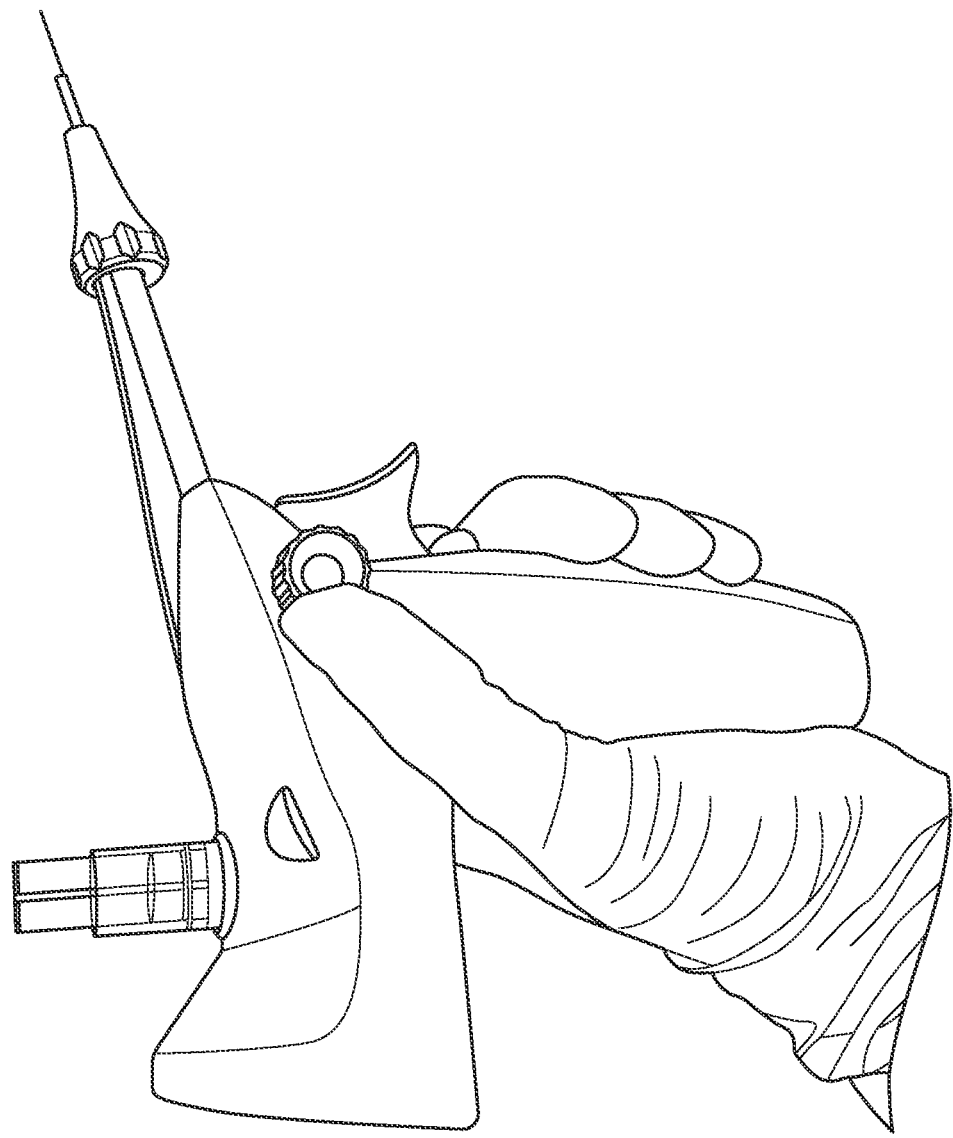
FIG. 15 shows an embodiment of a prototype of an endoscope with a user advancing the needle using a button (a thumb wheel) in accordance with the present disclosure.
Figure 16:
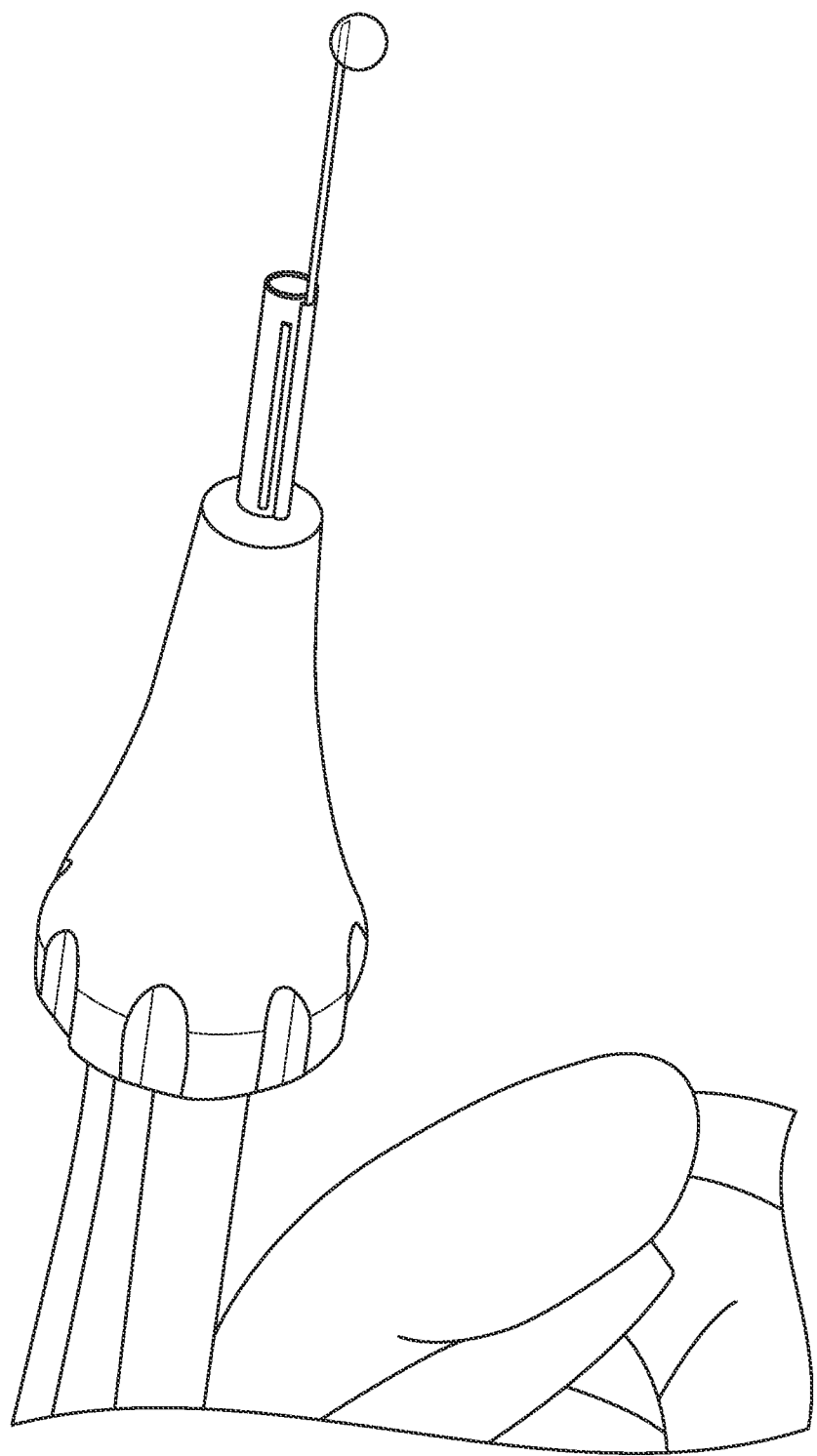
FIG. 16 shows an embodiment of a prototype of an endoscope dispensing a composition through its needle, in accordance with the present disclosure.

In one non-limiting example, a prototype of an embodiment of an endoscope as described herein was made using acrylonitrile butadiene styrene (ABS) plastic, fabricated by fused deposition modeling (FDM) 3D printing. The prototype included a 3D-printed handle and 3D-printed needle attachment. The screen size used for the mock-up is 1.5 inches in diameter. Commercial off-the-shelf parts were used for the pump, tubing, and gears for the rack and pinion. A steel rod with a 2.7 mm outer diameter was used to represent the rigid scope of the endoscope. The reservoir comprised a portion of a 10-mL plastic syringe with a luer-lock tip and a plunger, and the reservoir was attached externally to the device. The trigger was connected to a piston for the pump, and is spring-loaded. The disposable needle was a 27 gauge with a beveled tip. A rack and pinion mechanism was used to deploy and retract the needle. The pinion was paired to the thumb wheels, which were used to move the needle, and the rack was connected to the needle. FIG. 14A shows this prototype with its needle retracted, and FIG. 14B shows the prototype of FIG. 14A with its needle deployed. FIG. 15 shows the prototype with a user advancing and/or retracting the needle using a thumb wheel. FIG. 16 shows the prototype dispensing a composition through its needle.

Example 2

Figure 17A:
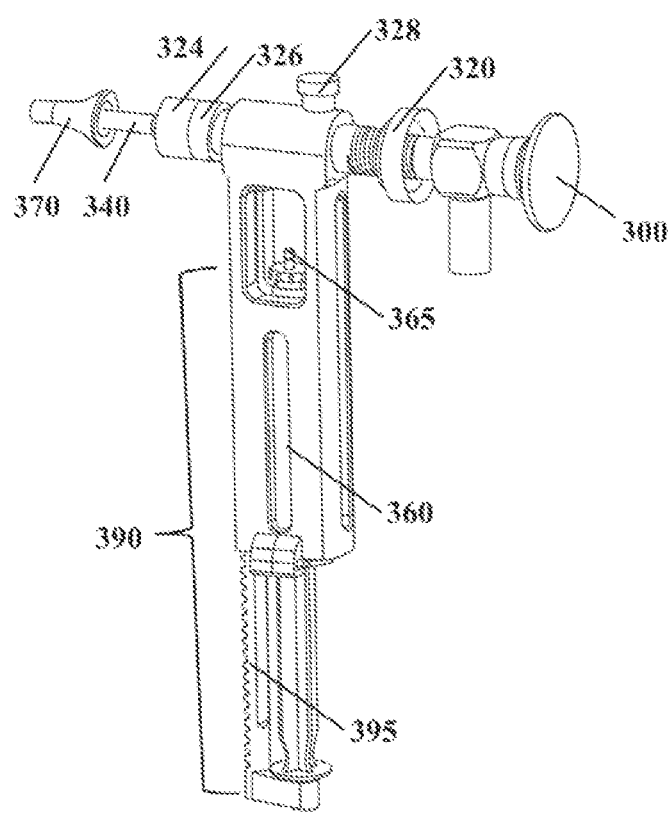
FIG. 17A shows an embodiment of a prototype of an endoscope, in accordance with the present disclosure.
Figure 17B:
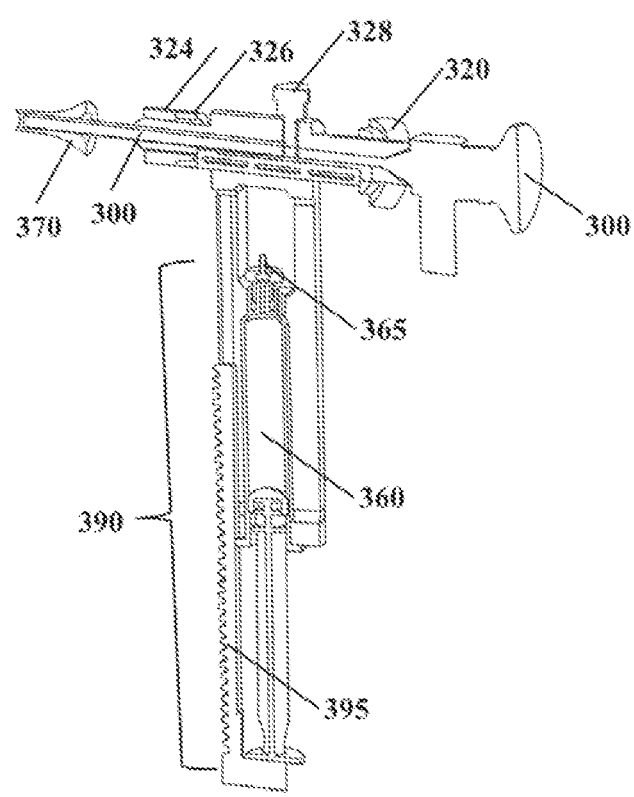
FIG. 17B shows a cross-section of the embodiment of the prototype of the endoscope of FIG. 17A, in accordance with the present disclosure.

In another non-limiting example, a second prototype of an embodiment of an endoscope as described herein was made. FIG. 17A shows a functional layout of the second prototype, and FIG. 17B shows its cross-section. The prototype shown in FIG. 17A and FIG. 17B comprises an endoscope 300, a knob 320 (i.e., button) configured to advance and/or retract the needle, a needle locking mechanism comprising a stop 324 and a stop collar 326, a scope locking mechanism 328, an elongated shaft 340, a reservoir 360 comprising a disposable syringe having a luer hub 365, a stop component 370, and a dispensing mechanism 390 comprising a gear rack 395.

Figure 17C:
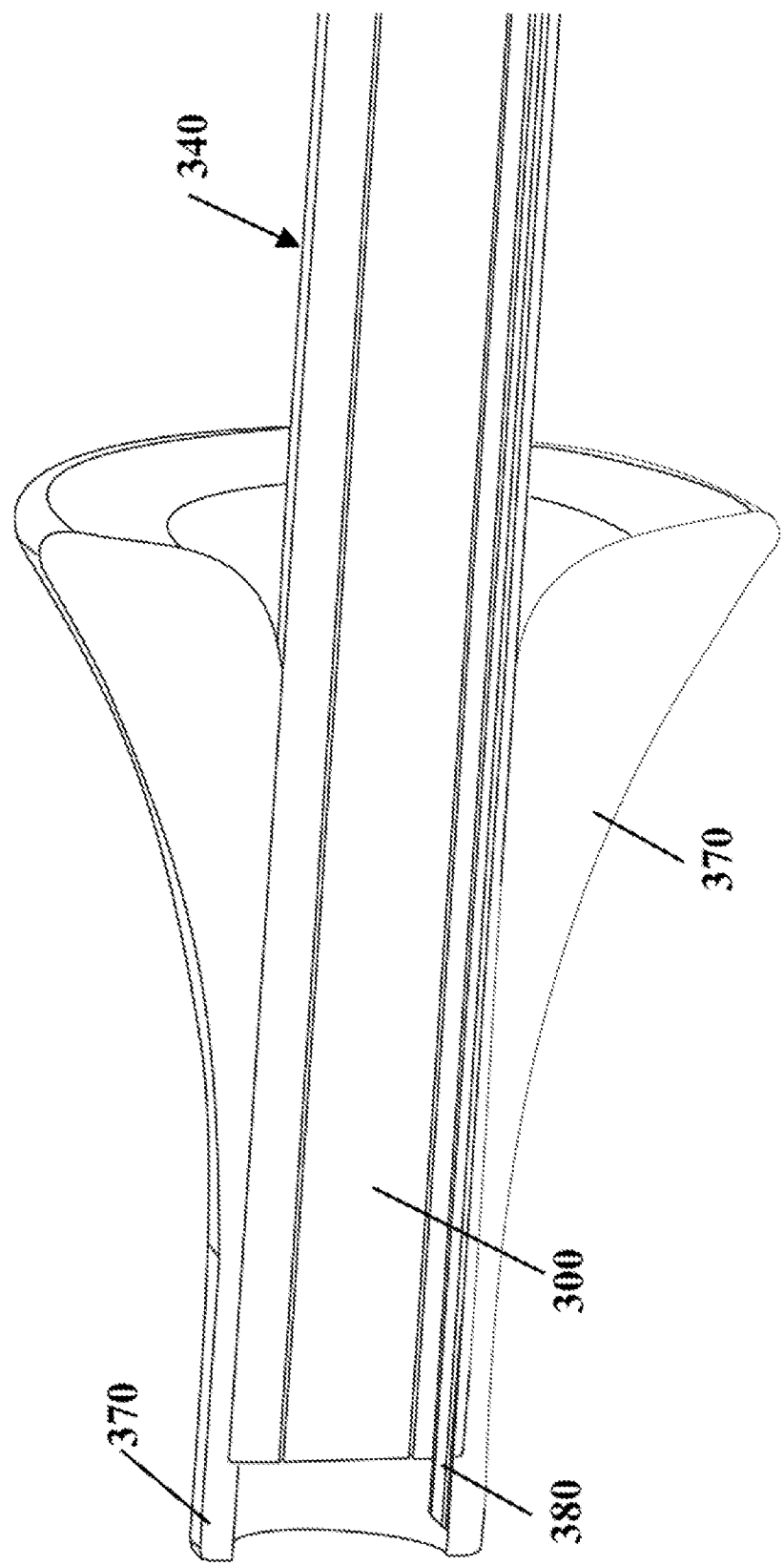
FIG. 17C shows a close-up cross-sectional view of a portion of the endoscope of FIG. 17A, in accordance with the present disclosure.

FIG. 17C shows a close-up cross-sectional view of a portion of the second prototype. In particular, FIG. 17C shows the elongated shaft 340 comprising the endoscope 300, and the needle 380. FIG. 17C also shows a stop component 370, the edge of which extends beyond the edge of the endoscope 300. Similarly, FIG. 17D shows another close-up view of a portion of the second prototype. In particular, FIG. 17D shows the needle locking mechanism 322, which comprises the stop 324 and the stop collar 326.

Figure 17E:
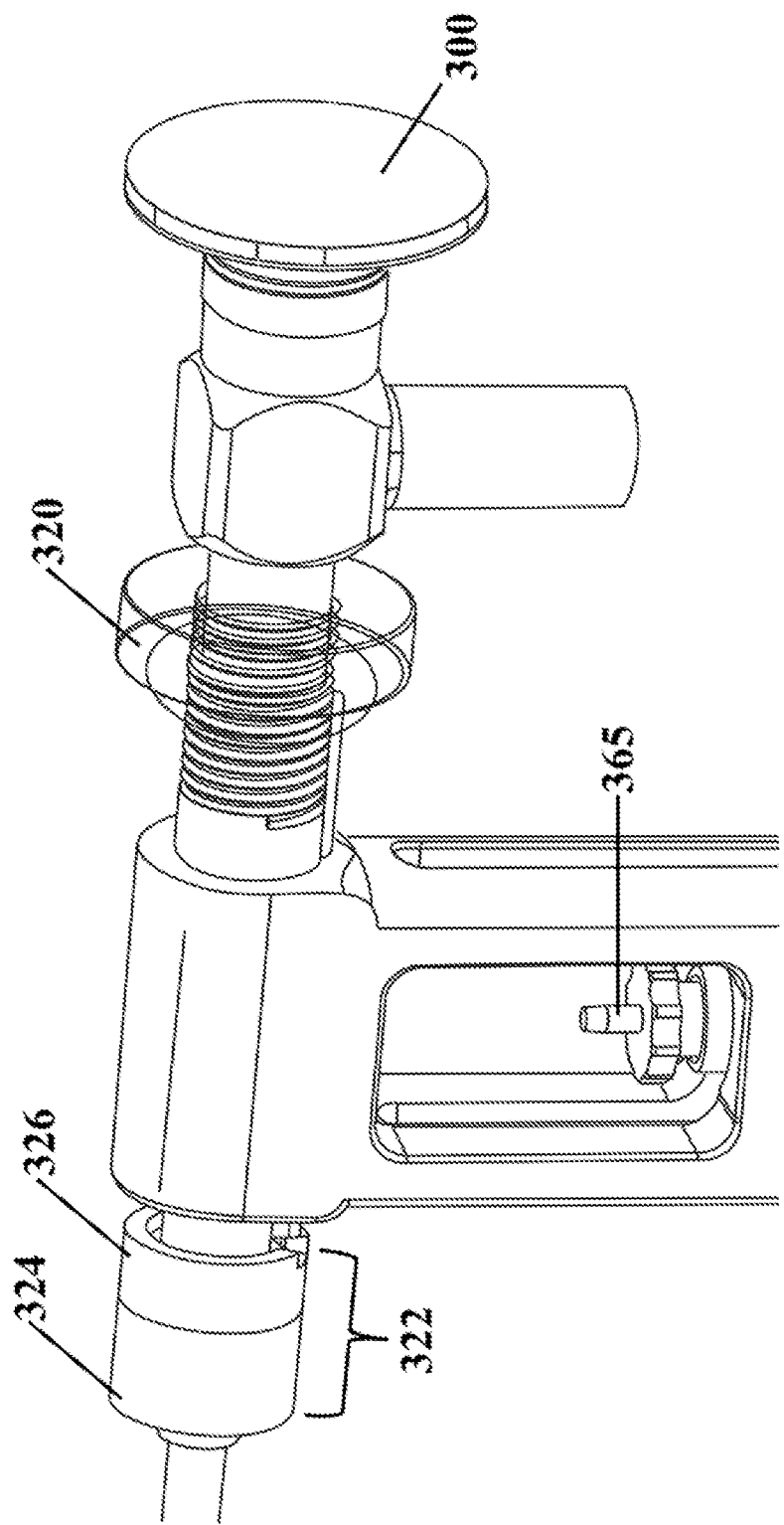
FIG. 17E shows another close-up view of a portion of the endoscope of FIG. 17A, in accordance with the present disclosure.
Figure 17F:
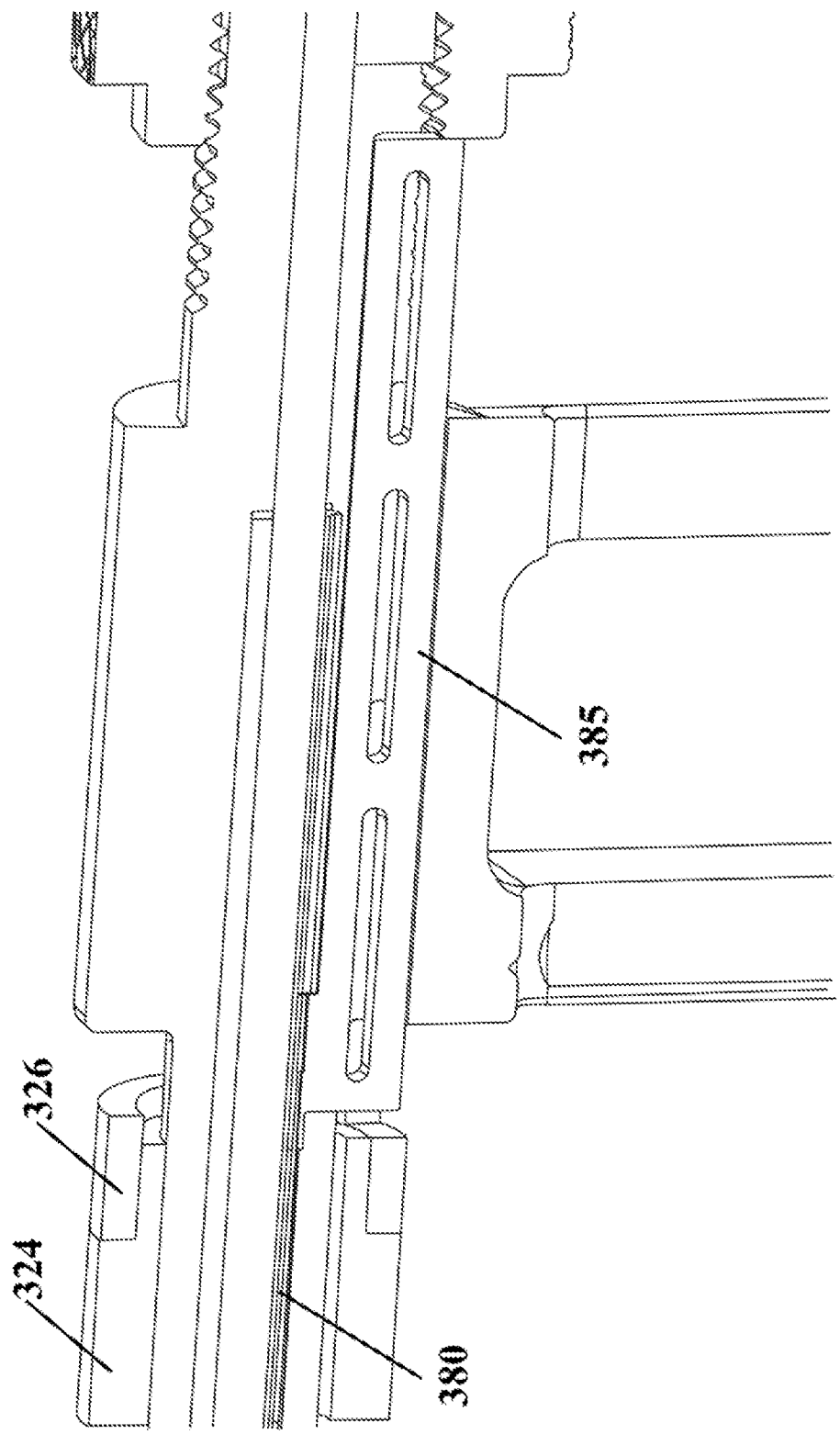
FIG. 17F shows a close-up cross-sectional view of a portion of the endoscope of FIG. 17A, in accordance with the present disclosure.

FIG. 17E also shows a close-up view of a portion of the second prototype. FIG. 17E includes the endoscope 300, the knob 320 (i.e., button) configured to advance and/or retract the needle, the needle locking mechanism 322, which comprises the stop 324 and the stop collar 326, and the luer hub 365 of the reservoir comprising a disposable syringe. FIG. 17F shows a close-up cross-sectional view of a portion of the second prototype. In particular, FIG. 17F shows the stop 324 and stop collar 326, the needle 380, and a sliding bar 385.

In the prototype shown in FIG. 17A, FIG. 17B, FIG. 17C, FIG. 17D, FIG. 17E, and FIG. 17F, the endoscope 300 is a Hopkins-style rigid endoscope, and the needle 380 is a 27-gauge needle. The prototype is designed to use a standard 5 mL disposable syringe as the reservoir 360. In a use scenario, a syringe is removed from a sterile package and used to draw a composition (e.g., a liquid containing one or more drugs) from a vial. The use of a sterile syringe (and its replacement with each exposure to a different composition) reduces or eliminates cross-contamination risks between syringes, compositions, and any containers or vials in which the composition(s) may be stored. Next, the syringe is primed by holding it upright, tapping, and pushing the plunger up to remove any trapped air. The primed syringe is then clipped to the device. The syringe is capped with a plastic luer hub 365 to connect the syringe to a needle 380 housed in the device using flexible tubing (not shown). The luer hub is custom-made by overmolding, because a standard 27-gauge needle luer hub is too large to be compatible with the device. The 27-gauge needle, tubing, luer hub, and syringe are all sterile and disposable. The composition is delivered in a precise and controlled manner, using the rail-climbing mechanism of the gear rack 395, similar to the mechanism of a one-handed bar clamp, to push the plunger of the syringe upward. One trigger will move the plunger of the syringe by about 0.25 mm (i.e., one tooth of the gear rack), which will deliver 25 μL of the composition from the 5 mL syringe.

In the prototype shown in FIG. 17A, FIG. 17B, FIG. 17C, FIG. 17D, FIG. 17E, and FIG. 17F, the endoscope 300 and the 27-gauge needle 380 are housed in an elongated shaft 340 having a 5 mm outer diameter. A disposable stop component 370 is put over the end of the elongated shaft, and the elongated shaft is recessed between 2 mm and 3.5 mm from the end of the stop component. The viewing angle of the endoscope of this prototype was measured to be 70°; having the stop component extend 2 mm from the tip of the endoscope does not obstruct the view of the endoscope and will help protect the endoscope tip from ear wax and other buildup. The inner diameter of the stop component is 5 mm, and the outer diameter is 6 mm. The inner layer of the stop component comprises a hard plastic, which provides some rigidity and makes it easy to place the stop component onto the elongated shaft. The outer portion of the stop component comprises a compressible or crushable material to conform to an ear canal and provide stability.

In the prototype shown in FIG. 17A, FIG. 17B, FIG. 17C, FIG. 17D, FIG. 17E, and FIG. 17F, the needle 380 is advanced using the knob 320 (i.e., button) configured to advance and/or retract the needle, wherein the knob is a concentric needle advancement knob based on a screw actuator mechanism. When the knob is rotated, its bushing pushes the sliding bar 385, shown in FIG. 17F, which moves the needle 380. The needle locking mechanism 322, which comprises a stop 324 and a stop collar 326, moves along with the needle 380. When the needle 380 touches the tympanic membrane of an ear, a user can rotate the stop collar 326 of the needle locking mechanism 322 to stop the movement of the needle 380. Then, the sliding bar 385 can only advance about 1.5 mm, governed by the gap between the sliding bar 385 and the stop collar 326, limiting how far the needle can advance past the tympanic membrane as an added safety feature. In this prototype, the knob 320 and stop collar 326 require two-handed operation, with one hand holding the device and the other hand rotating either the knob 320 or the stop collar 326. In other embodiments, however, modifications may be made to allow for one-handed operation. For example, the needle advancement mechanism shown in FIG. 7B comprises two wheels 120, which can be reached and manipulated by a user's thumb. The wheels of FIG. 7B are coupled to each other, such that either can advance or retract the needle, and the user can choose the wheel based on his or her right- or left-handedness. Similarly, the knob 320 of FIG. 17A, FIG. 17B, and FIG. 17E may be modified to comprise two wheels, like those used in FIG. 7B, while the other mechanisms are maintained. Furthermore, the stop collar 326 of the second prototype may be modified so that it can be locked using the hand holding the device. Having the ability to hold and control all functions with a single hand will provide more stable operation. When a user's dominant hand holds the device and manipulates it, the other hand can be used to further stabilize the device.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

The invention claimed is:

1. An otoscope comprising:
   a needle and a scope;

a handle comprising at least one button;
a visualization component;
a reservoir configured to contain a composition; and
a dispensing mechanism;
a needle advancement and retraction mechanism for controlling insertion and removal of the needle;
wherein the at least one button, the needle, the reservoir, and the dispensing mechanism are operably linked to cause the composition to be dispensed from the reservoir through the needle to a portion of an ear; and
wherein the at least one button of the handle is configured to dispense the composition from the reservoir through the needle to the portion of the ear at a controlled rate.

2. The otoscope of claim 1, wherein at least one of the needle, the scope, the reservoir, and the dispensing mechanism are housed in an elongated shaft.

3. The otoscope of claim 2, wherein the elongated shaft further comprises a sponge applicator.

4. The otoscope of claim 2, further comprising a sensor configured to detect the puncture of the portion of the ear.

5. The otoscope of claim 4, wherein the sensor is selected from the group consisting of a miniature acoustic sensor, a microphone, a pressure sensor, a surface acoustic wave pressure sensor, a capacitive touch sensor, a vibrational sensor, a spring-loaded pressure sensor, and combinations thereof.

6. The otoscope of claim 4, wherein the sensor is placed in a location selected from the group consisting of along the needle, at the needle tip, and along the elongated shaft.

7. The otoscope of claim 1, wherein the scope comprises at least one lens and a fiber optic light transmission component.

8. The otoscope of claim 1, wherein the reservoir and the dispensing mechanism are contained within the handle.

9. The otoscope of claim 1, wherein the at least one button, the needle, the reservoir, and the dispensing mechanism are linked by a mechanism selected from the group consisting of an electronic link, a mechanical link, and an electromechanical link.

10. The otoscope of claim 1, wherein the at least one button facilitates a function selected from the group consisting of advancing the needle, retracting the needle, dispensing the composition, and combinations thereof, and wherein the at least one button is selected from the group consisting of a push-button, a wheel, a trigger, and combinations thereof.

11. The otoscope of claim 1, wherein the scope comprises a component selected from the group consisting of a fiber optic cable, a digital imaging chip, and a sensor.

12. The otoscope of claim 1, wherein the scope is selected from the group consisting of an optical scope and a digital scope.

13. The otoscope of claim 1, wherein visualization component is coupled to the scope by a mechanism selected from the group consisting of an optical link, an electronic link, and an opto-electronic link.

14. The otoscope of claim 1, further comprising a stop component removably coupled to an elongated shaft.

15. The otoscope of claim 1, wherein the visualization component is selected from the group consisting of a lens, an eye piece, a display, a monitor, a computer, a phone, a tablet, a smart device, and combinations thereof.

16. The otoscope of claim 1, wherein the dispensing mechanism is selected from the group consisting of a spring-loaded mechanism, a sliding rod mechanism, a piston, an air pressurized mechanism, a pump, a peristaltic pump, a positive displacement pump, a syringe pump, a diaphragm metering pump, and combinations thereof.

17. The otoscope of claim 1, wherein the at least one button of the handle is configured to adjust the controlled rate.

18. The otoscope of claim 1, wherein the composition is selected from the group consisting of air, water, an anesthetic, phenol, an anti-inflammatory composition, a biologic, a protein, a peptide, a gene delivery system, a steroid, an antibiotic, a small molecule, and combinations thereof.

19. The otoscope of claim 1, further comprising a straight laser configured to indicate a target location in the portion of the ear, and an angled laser configured to determine a distance to the portion of the ear.

20. A method for using an otoscope, the method comprising:
inserting into a portion of an ear an otoscope comprising:
    a needle and a scope;
    a handle comprising at least one button and a visualization component;
    a reservoir configured to contain a composition; and
    a dispensing mechanism;
    and a needle advancement and retraction mechanism for controlling insertion and removal of the needle;
wherein the at least one button, the needle, the reservoir, and the dispensing mechanism are operably linked to cause the composition to be dispensed from the reservoir through the needle to the portion of the ear; and wherein the at least one button of the handle is configured to dispense the composition from the reservoir through the needle to the portion of the ear at a controlled rate;
    using the visualization component to visualize the portion of the ear;
    and pressing the at least one button to dispense the composition from the reservoir through the needle to the portion of the ear.

* * * * *